United States Patent [19]

Takagawa et al.

[11] Patent Number: 4,610,983
[45] Date of Patent: Sep. 9, 1986

[54] N-ACYL ACIDIC AMINO ACID DIAMIDE DERIVATIVE, A SALT THEREOF, AND AN ANTI-ULCER AGENT CONTAINING THE SAME

[75] Inventors: Noboru Takagawa; Shiro Hirai; Takuya Kodama, all of Toyama; Hiroshi Hirano, Koyabe; Yasuo Kiba, Toyama; Mikio Kawabata, Kurobe; Tatsuya Miyaura; Yasuyuki Suzuki, both of Toyama, all of Japan

[73] Assignee: Toyama Chemical Co., Ltd., Tokyo, Japan

[21] Appl. No.: 677,466

[22] Filed: Dec. 3, 1984

[30] Foreign Application Priority Data

Jun. 12, 1984 [JP] Japan .................. 59-120584

[51] Int. Cl.[4] .............. A61K 31/34; A61K 31/16; C07D 307/54; C07C 103/147
[52] U.S. Cl. .................. 514/230; 549/68; 549/76; 514/234; 549/77; 549/283; 514/255; 549/288; 549/404; 514/316; 549/407; 549/463; 514/320; 549/467; 514/326; 549/494; 514/422; 549/496; 514/457; 514/443; 514/444; 514/459; 514/469; 514/471; 514/472; 544/85; 544/86; 544/130; 544/141; 544/145; 544/146; 544/147; 546/187; 546/208; 546/196; 546/202; 546/207; 546/212; 546/214; 548/517; 548/524; 548/527; 549/57; 549/58
[58] Field of Search .............. 549/57, 58, 68, 76, 549/77, 283, 288, 404, 407, 463, 467, 494, 496; 548/524, 517, 527; 546/187, 208, 196, 202, 207, 212, 214; 544/85, 86, 130, 141, 145, 146, 147; 514/230, 234, 255, 316, 320, 326, 422, 457, 443, 444, 459, 469, 471, 472

[56] References Cited

U.S. PATENT DOCUMENTS

4,143,070 3/1979 Walker .................. 564/152
4,517,378 5/1985 Vasta .................... 564/160

*Primary Examiner*—Richard L. Raymond
*Attorney, Agent, or Firm*—Oblon, Fisher, Spivak, McClelland & Maier

[57] ABSTRACT

This invention relates to a novel N-acyl acidic amino acid diamide derivative represented by the general formula or a salt thereof:

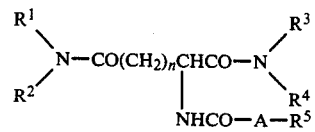

wherein each of $R^1$, $R^2$, $R^3$ and $R^4$, which may be the same or different, represents a hydrogen atom or a substituted or unsubstituted alkyl, cycloalkyl, alkenyl or aralkyl group, or $R^1$ and $R^2$ and/or $R^3$ and $R^4$, when taken together with the respective adjacent nitrogen atoms, form a substituted or unsubstituted heterocyclic group; $R^5$ represents a substituted or unsubstituted cycloalkyl, acyl or heterocyclic group; A represents a bond or a substituted or unsubstituted alkylene, alkenylene or alkadienylene group; and n is 1, 2 or 3. Said compound has an anti-ulcer activity which is effective to human beings and animals. This disclosure relates to such a compound, to a process for the production thereof and to an anti-ulcer agent containing the same.

22 Claims, No Drawings

N-ACYL ACIDIC AMINO ACID DIAMIDE DERIVATIVE, A SALT THEREOF, AND AN ANTI-ULCER AGENT CONTAINING THE SAME

This invention relates to a novel N-acyl acidic amino acid diamide derivative, a salt thereof, a process for producing the same and an anti-ulcer agent containing the same.

Conventionally, L-glutamine has widely been used as an anti-ulcer agent, but in recent years, acylglutamic acid derivatives have been developed as its modifications and have come to be used for curing ulcers. However, the anti-ulcer activities of the acylglutamic acid derivatives are not sufficient, and a compound having a greater anti-ulcer activity and a high efficiency has been desired to be developed.

Under these circumstances, in order to find a compound having a greater anti-ulcer activity, the present inventors have devoted themselves to investigation, and have consequently found a compound represented by the general formula (I) having a greater anti-ulcer activity and satisfying the objects and a process for producing the same, whereby this invention has been accomplished.

An object of this invention is to provide a novel N-acyl acidic amino acid diamide derivative and a salt thereof which have an anti-ulcer activity.

Another object of this invention is to provide a process for producing a novel N-acyl acidic amino acid diamide derivative or a salt thereof.

A further object of this invention is to provide an anti-ulcer agent containing a novel N-acyl acidic amino acid diamide derivative or a salt thereof as an active ingredient.

Other objects and advantages of this invention will become apparent from the following description.

The compounds of this invention are novel N-acyl acidic amino acid diamide derivatives represented by the general formula (I) and salts thereof:

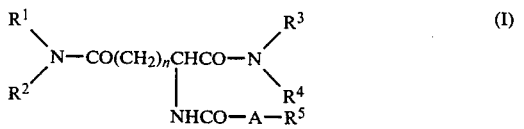

wherein each of $R^1$, $R^2$, $R^3$ and $R^4$, which may be the same or different, represents a hydrogen atom or a substituted or unsubstituted alkyl, cycloalkyl, alkenyl or aralkyl group or $R^1$ and $R^2$ and/or $R^3$ and $R^4$, when taken together with the respective adjacent nitrogen atoms, form a substituted or unsubstituted heterocyclic group; $R^5$ represents a substituted or unsubstituted cycloalkyl, acyl or heterocyclic group; A represents a bond or a substituted or unsubstituted alkylene, alkenylene or alkadienylene group; and n is 1, 2 or 3.

This invention is explained below in detail.

In the general formula (I), the alkyl groups for $R^1$, $R^2$, $R^3$ and $R^4$ include $C_{1-8}$ alkyl groups such as methyl, ethyl, n-propyl, isopropyl, n-butyl, isobutyl, sec.-butyl, tert.-butyl, pentyl, hexyl, heptyl, octyl and the like, the cycloalkyl groups for $R^1$, $R^2$, $R^3$ and $R^4$ includes $C_{3-7}$ cycloalkyl groups such as cyclopropyl, cyclobutyl, cyclopentyl, cyclohexyl, cycloheptyl and the like; the alkenyl groups for $R^1$, $R^2$, $R^3$ and $R^4$ include $C_{2-4}$ alkenyl groups such as vinyl, allyl, isopropenyl, butenyl and the like; the aralkyl groups for $R^1$, $R^2$, $R^3$ and $R^4$ include ar-$C_{1-4}$alkyl groups such as benzyl, phenethyl, naphthylmethyl and the like.

The heterocyclic group which $R^1$ and $R^2$ form when taken together with the adjacent nitrogen atom may further contain at least one hetero atom selected from nitrogen atom, sulfur atom and oxygen atom, and includes, for example, pyrrolidinyl, piperidyl, piperazinyl, morpholinyl and the like.

The heterocyclic group which $R^3$ and $R^4$ form when taken together with the adjacent nitrogen atom may further contain at least one hetero atom selected from nitrogen atom, sulfur atom and oxygen atom and includes, for example, pyrrolidinyl, piperidyl, piperazinyl, morpholinyl and the like.

The cycloalkyl groups for $R^5$ include $C_{3-7}$cycloalkyl groups such as cyclopropyl, cyclobutyl, cyclopentyl, cyclohexyl, cycloheptyl and the like. The heterocyclic groups for $R^5$ include 5-membered ring, 6-membered ring or fused ring type heterocyclic group containing at least one hetero atom selected from nitrogen atom, sulfur atom and oxygen atom, the 5-membered ring type heterocyclic groups including, for example, thienyl, furyl, pyrrolyl, imidazolyl, pyrazolyl, thiazolyl, isothiazolyl, oxazolyl, isoxazolyl, pyrrolidinyl, pyrrolinyl, imidazolidinyl, imidazolinyl, pyrazolidinyl, tria zolyl, tetrazolyl, tetrahydrofuryl and the like; the 6-membered ring type heterocyclic groups including, for example, pyranyl, pyridyl, pyrazinyl, pyrimidinyl, pyridazinyl, piperidyl, piperazinyl, morpholinyl, triazinyl, thiazinyl and the like; the fused ring type heterocyclic groups including, for example, benzothienyl, benzofuryl, isobenzofuryl, indolyl, isoindolyl, indazolyl, purinyl, quinolyl, isoquinolyl, naphthyridinyl, quinoxadinyl, chromanyl, indolinyl, isoindolinyl, chromenyl, 3,6-epoxy-1-cyclohexenyl and the like. The acyl groups for $R^5$ means, for example, $C_{1-5}$ alkanoyl groups such as acetyl, propionyl, butyryl and the like; aroyl groups such as benzoyl, naphthoyl and the like; and heterocyclic carbonyl groups having any of the heterocyclic groups described right above.

The alkyl, cycloalkyl, alkenyl and aralkyl groups for $R^1$, $R^2$, $R^3$ and $R^4$, the heterocyclic groups which $R^1$ and $R^2$ form when taken together with the adjacent nitrogen atom, the heterocyclic groups which $R^3$ and $R^4$ form when taken together with the adjacent nitrogen atom, and the cycloalkyl, acyl and heterocyclic groups for $R^5$ may each be substituted by at least one substituent selected from halogen atoms such as fluorine atom, chlorine atom, bromine atom, iodine atom and the like; hydroxyl group; amino group; carboxyl group; $C_{1-8}$alkyl groups such as methyl, ethyl, n-propyl, isopropyl, n-butyl, isobutyl, sec.-butyl, tert.-butyl, pentyl, hexyl, heptyl, octyl and the like; oxo group; $C_{1-8}$alkoxy groups such as methoxy, ethoxy, n-propoxy, isopropoxy, n-butoxy, isobutoxy, sec.-butoxy, tert.-butoxy, pentyloxy, hexyloxy, heptyloxy, octyloxy and the like; aryl or halogen-substituted aryl groups such as phenyl, naphthyl, chlorophenyl and the like; ar-$C_{1-4}$alkyl or alkoxy-substituted ar-$C_{1-4}$alkyl groups such as benzyl, phenethyl, naphthylmethyl, (2,3,4- or 3,4,5-)trimethoxybenzyl and the like; amino-$C_{1-4}$alkyl groups such as aminomethyl, aminoethyl and the like; di-$C_{1-4}$alkylamino-$C_{1-4}$alkyl groups such as dimethylaminomethyl, diethylaminoethyl and the like; (4-methylpiperazin-1-yl)methyl group; hydroxy-substituted $C_{1-4}$alkyl groups such as hydroxymethyl, hydroxyethyl and the like; $C_{1-5}$alkanoyloxy groups such as acetoxy, propionyloxy, butyryloxy and the like; ar-C$_{2-4}$alkenylcarbonyl or alkoxy-substituted ar-C$_{2-4}$alkenylcarbonyl groups such as styrylcarbonyl, 3,4,5-trimethoxystyrylcarbonyl and the like; ar-C$_{1-4}$alkyloxycarbonylamino groups such as benzyloxycarbonylamino and the like; ar-C$_{1-4}$alkyloxycarbonylamino-C$_{1-4}$alkyl groups such as benzyloxycarbonylaminomethyl and the like; aroylamino or alkoxy-substituted aroylamino groups such as benzoylamino, 3,4,5-trimethoxybenzoylamino and the like; and heterocyclic carbonylalkyl groups such as pyrrolidinylcarbonylmethyl, piperidylcarbonylmethyl, piperazinylcarbonylmethyl, morpholinylcarbonylmethyl and the like; etc.

The alkylene groups for A include C$_{1-5}$alkylene groups such as methylene, ethylene, propylene, trimethylene, tetramethylene and the like. The alkenylene groups for A include C$_{2-5}$alkenylene groups such as vinylene, propenylene, butenylene, and the like. The alkadienylene groups for A include C$_{4-6}$alkadienylene groups such as 1,3-butadienylene and the like. These groups may each be substituted by at least one substituent selected from C$_{1-8}$alkyl groups such as methyl, ethyl, propyl, butyl and the like; hydroxyl group; and aryl groups such as phenyl, naphthyl and the like.

When the compound of the general formula (I) has a carboxyl group, a hydroxyl group and/or an amino group, these groups may be protected with conventional protecting groups.

Here, the protecting group for the hydroxyl group includes all groups which can conventionally be used as protecting groups for a hydroxyl group, and there may be exemplified, for example, easily removable acryl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 8-quinolyloxycarbonyl, trifluoroacetyl and the like, as well as benzyl, trityl, methoxymethyl, o-nitrophenylthio, 2,4-dinitrophenylthio, etc.

The protecting group for the amino group includes all groups which can conventionally be used as protecting groups for an amino group, and there may be exemplified, for example, easily removable acyl groups such as 2,2,2-trichloroethoxycarbonyl, 2,2,2-tribromoethoxycarbonyl, benzyloxycarbonyl, methanesulfonyl, benzenesulfonyl, p-toluenesulfonyl, p-nitrobenzyloxycarbonyl, p-bromobenzyloxycarbonyl, (mono-, di- or tri-)chloroacetyl, trifluoroacetyl, acetyl, formyl, tert.-amyloxycarbonyl, methoxycarbonyl, ethoxycarbonyl, 2-cyanoethoxycarbonyl, tert.-butoxycarbonyl, methoxymethoxycarbonyl, acetylmethoxycarbonyl, p-methoxybenzyloxycarbonyl, phenoxycarbonyl, 3,4-dimethoxybenzyloxycarbonyl, 4-(phenylazo)benzyloxycarbonyl, 4-(4-methoxyphenylazo)benzyloxycarbonyl, (pyridine-1-oxide-2-yl)methoxycarbonyl, 2-furfuryloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl, benzoyl, p-nitrobenzoyl, p-tert.-butylbenzoyl and the like, as well as easily removable groups such as trityl, benzyl, p-nitrobenzyl, o-nitrophenylthio, 2,4-dinitrophenylthio, benzylidene, p-nitrobenzylidene, 2-hydroxybenzylidene, 2-hydroxy-5-chlorobenzylidene, (2-hydroxynaphthalen-1-yl)methyl, (3-hydroxypyridin-4-yl)methyl, 1-ethoxycarbonyl-1-propen-2-yl, 1-morpholinocarbonyl-1-propen-2-yl, 1-diethylaminocarbonyl-1-propen-2-yl, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene and the like; and other protecting groups for an amino group such as di- or tri-alkylsilyl and the like. Further, the protecting group for the carboxyl group includes all groups which can usually be used as a carboxyl-protecting groups, and there may be exemplified, for example, groups such as methyl, ethyl, n-propyl, isopropyl, n-butyl, tert.-butyl, phenyl, indanyl, benzyl, phenethyl, diphenylmethyl, trityl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, 2,2,2-trichloroethyl, 1,1-dimethyl-2-propenyl, 1,1-dimethylpropyl, acetoxymethyl, propionyloxymethyl, pivaloyloxymethyl, 1-acetylethyl, 1-pivaloyloxyethyl, 1-pivaloyloxy-n-propyl, acetylthiomethyl, pivaloylthiomethyl, 1-acetylthioethyl, 1-pivaloylthioethyl, methoxymethyl, ethoxymethyl, n-propoxymethyl, isopropoxymethyl, n-butoxymethyl, methoxycarbonyloxymethyl, ethoxycarbonyloxymethyl, tert.-butoxycarbonyloxymethyl, 1-methoxycarbonyloxyethyl, 1-ethoxycarbonyloxyethyl, 1-isopropoxycarbonyloxyethyl, phthalidyl, 2-(phthalidylidene)ethyl, 2-(5-fluorophthalidylidene)ethyl, 2-(6-chlorophthalidylidene)ethyl, 2-(6-methoxyphthalidylidene)ethyl, 5-methyl-2-oxo-1,3-dioxol-4-yl, 5-ethyl-2-oxo-1,3-dioxo-4-yl, 5-propyl-2-oxo-1,3-dioxol-4-yl, 1,1-dimethyl-2-propenyl, 3-methyl-3-butenyl, succinimidomethyl, 1-cyclproplethyl, methylthiomethyl, phenylthiomethyl, dimethylaminomethyl, (quinoline-1-oxide-2-yl)methyl, (pyridine-1-oxide-2-yl)methyl, bis(p-methoxyphenyl)methyl and the like. Further, the carboxyl group may be protected with a non-metallic compound such as titanium tetrachloride or the like, or with, for example, a silyl compound such as dimethylchlorosilane or the like as described in Japanese Patent Application Kokai (Laid-Open) No. 7,073/71 and Dutch Patent Application (Laid-Open) No. 7,105,259.

The salts of compound represented by the general formula (I) include conventionally known salts at basic groups such as an amino group and salts at acidic groups such as a carboxyl group. Here, the salts at acidic groups include, for example, salts with alkali metals such as sodium, potassium and the like; salts with alkaline earth metals such as magnesium, calcium and the like; ammonium salts; salts with nitrogen-containing organic bases such as procaine, dibenzylamine, N-benzyl-β-phenethylamine, 1-ephenamine, N,N-dibenzylethylenediamine, triethylamine, trimethylamine, tributylamine, pyridine, N,N-dimethylaniline, N-methylpiperidine, N-methylmorpholine, diethylamine, dicyclohexylamine and the like. The salts at basic groups include, for example, salts with mineral acids such as hydrochloric acid, hydrobromic acid, sulfuric acid and the like; salts with organic carboxylic acids such as oxalic acid, succinic acid, formic acid, trichloroacetic acid, trifluoroacetic acid and the like; salts with sulfonic acids such as methanesulfonic acid, ethanesulfonic acid, benzene-sulfonic acid, toluene-2-sulfonic acid, toluene-4-sulfonic acid, mesitylenesulfonic acid (2,4,6-trimethylbenzenesulfonic acid), naphthalene-1-sulfonic acid, naphthalene-2-sulfonic acid, phenylmethanesulfonic acid, benzene-1,3-disulfonic acid, toluene-3,5-disulfonic acid, naphthalene-1,5-disulfonic acid, naphthalene-2,6-disulfonic acid, naphthalene-2,7-disulfonic acid, benzene-1,3,5-trisulfonic acid, benzene-1,2,4-trisulfonic acid, naphthalene-1,3,5-trisulfonic acid and the like; etc.

The compound of the general formula (I) has an asymmetric carbon atom, and hence has D, L and DL configurations. When it has a double bond, it has cis-trans isomers, tautomers and the like, and these isomers and mixtures thereof are all included in this invention. Further, hydrates and solvates of the compound of the general formula (I) are also included in this invention.

According to this invention, the novel compound represented by the general formula (I) or a salt thereof which is useful as an anti-ulcer agent can be produced by any of the following production processes:

PRODUCTION PROCESS [A]

A process for producing a novel N-acyl amino acid diamide derivative represented by the general formula (I) or a salt thereof:

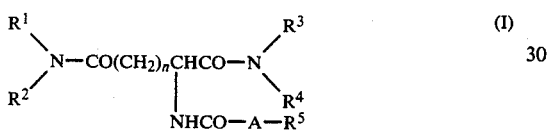

wherein $R^1$, $R^2$, $R^3$, $R^4$, $R^5$, A and n have the same meanings as defined above, which comprises reacting a compound represented by the general formula (II) or a salt thereof;

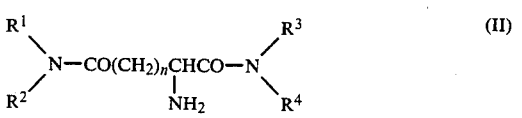

wherein $R^1$, $R^2$, $R^3$, $R^4$ and n have the same meanings as defined above, with a compound represented by the general formula (III) or a reactive derivative in the carboxyl group thereof:

wherein $R^5$ and A have the same meanings as defined above.

PRODUCTION PROCESS [B]

A process for producing a novel N-acyl amino acid diamide derivative represented by the general formula (I) or a salt thereof, which comprises reacting a compound represented by the general formula (IV) or a reactive derivative in the carboxyl group thereof;

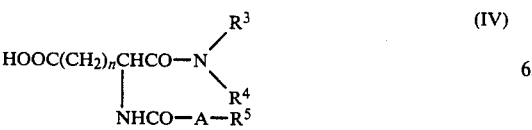

wherein $R^3$, $R^4$, $R^5$, A and n have the same meanings as defined above, with an amine represented by the general formula (V):

wherein $R^1$ and $R^2$ have the same meanings as defined above.

PRODUCTION PROCESS [C]

A process for producing a novel N-acyl amino acid diamide derivative represented by the general formula (I) or a salt thereof, which comprises reacting a compound represented by the general formula or a reactive derivative in the carboxyl group thereof:

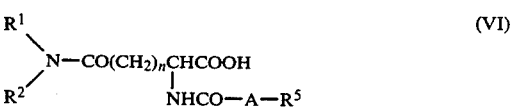

wherein $R^1$, $R^2$, $R^5$, A and n have the same meanings as defined above, with an amine represented by the general formula (VII):

wherein $R^3$ and $R^4$ have the same meanings as defined above.

PRODUCTION PROCESS [D]

A process for producing a novel N-acyl amino acid diamide derivative represented by the general formula (Ia) or a salt thereof:

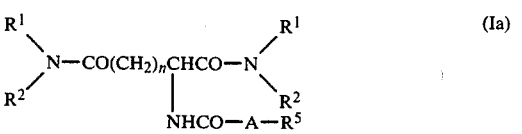

wherein $R^1$, $R^2$, $R^5$, A and n have the same meanings as defined above, which comprises reacting a compound represented by the general formula (VIII) or a reactive derivative in the carboxyl group thereof:

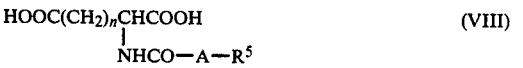

wherein $R^5$, A and n have the same meanings as defined above, with an amine represented by the general formula (V).

As the salt of the compound of the general formula (II), there may be exemplified salts with acids such as hydrochloric acid, hydrobromic acid and the like.

The compounds of the general formulas (II), (IV), (VI) and (VIII) which are the starting materials in the above-mentioned production processes [A], [B], [C] and [D], respectively, can be produced, for example, by the following reaction routes:

Process for producing the compound
of the general formula (II)

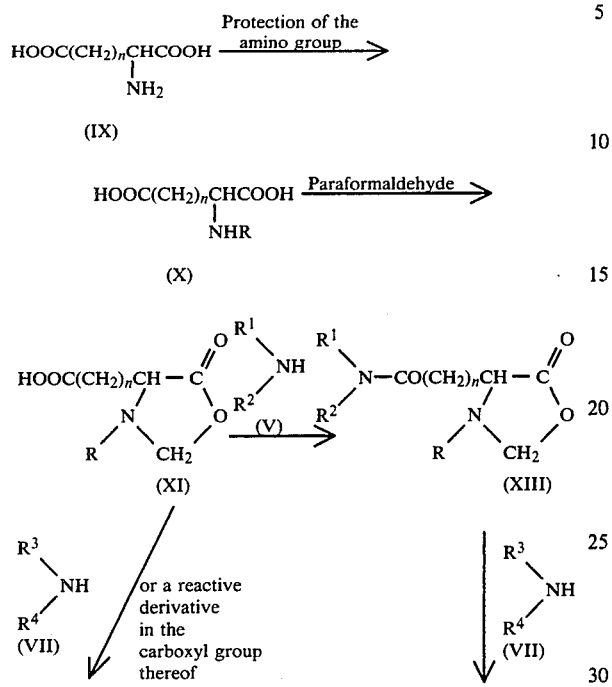

(XII) or a reactive derivative in the carboxyl group thereof

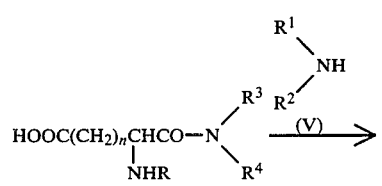

(XIV)

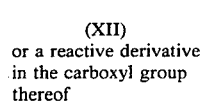

(II)

Process for producing the compound
of the general formulas (IV) and (VIII)

$$R^5-A-COOH$$
(III)

or a reactive derivative in the carboxyl group thereof

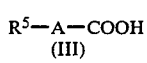

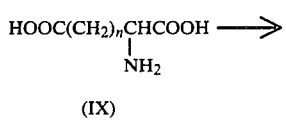

(IX)

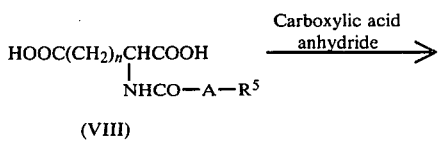

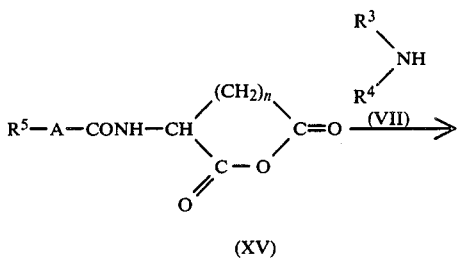

(XV)

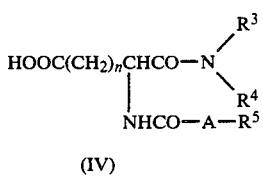

(IV)

Process for producing the compound
of the general formula (VI)

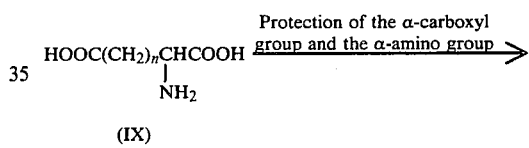

(IX)

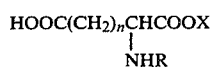

(XVI)

or a reactive derivative in the carboxyl group thereof

(V)

Removal of the α-carboxyl-protecting group and the α-amino-protecting group

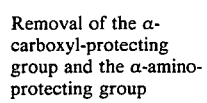

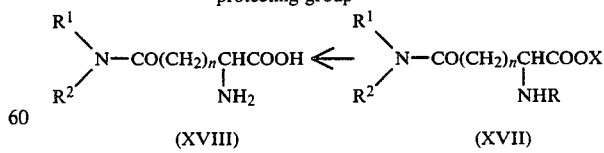

(XVIII)     (XVII)

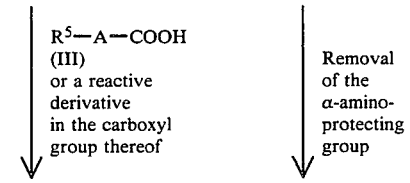

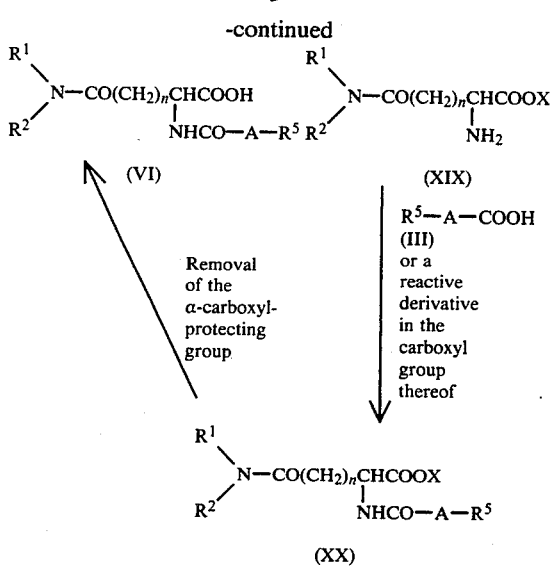

In the above reaction formulas, $R^1$, $R^2$, $R^3$, $R^4$, $R^5$, A and n have the same meanings as defined above; R represents an amino-protecting group; and X represents a carboxyl-protecting group.

As the carboxyl-protecting group for X, there may be exemplified those described as carboxyl-protecting group explained in compound (I) and particularly preferable ones arre alkyl groups such as methyl, ethyl, tert.-butyl and the like; aralkyl groups such as benzyl, phenethyl and the like; etc. As the amino-protecting group for R, there may be exemplified the same amino-protecting groups as described in compound (I) above.

Next, the processes for producing the compounds of this invention and the production steps of the starting materials are further explained below in more detail.

1. Process for producing the compound of the general formula (II) and the Production Process [A]

(1) A compound of the general formula (IX) (aspartic acid in the case of n being 1, glutamic acid in the case of n being 2, and 2-aminoadipic acid in the case of n being 3) is used as a starting material, and the amino group of the compound of the general formula (IX) is protected with an amino-protecting group used in usual synthesis of a peptide, for example, a benzyloxycarbonyl group, a substituted benzyloxycarbonyl group, a tosyl group or the like to obtain a compound of the general formula (X). The compound obtained is subjected to dehydrating condensation with paraformaldehyde in the presence of a catalyst such as p-toluenesulfonic acid, sulfuric acid or the like by using, as a solvent, a halogenated hydrocarbon such as chloroform, 1,1,2-trichloroethane or the like or an aromatic hydrocarbon such as benzene, toluene or the like, to obtain a compound of the general formula (XI). The amount of the catalyst to be added is preferably about 2 to 5% (volume/volume) based on the compound of the general formula (X), and this reaction is completed in 1 to 10 hours, though the time required for the completion varies a little depending on the solvent used.

The compound of the general formula (XI) or (XIII) is reacted with an amine of the general formula (VII) to obtain a compound of the general formula (XII) or (XIV), respectively. In this reaction, the amount of the amine of the general formula (VII) to be used is sufficiently about 2.5 moles or about 1.5 moles per mole of the compound of the general formula (XI) or (XIII), respectively, and as the solvent, there may be used those which do not adversely affect the reaction, for example, halogenated hydrocarbons such as chloroform, 1,1,2-trichloroethane and the like; esters such as ethyl acetate, butyl acetate and the like; ethers such as tetrahydrofuran, dioxane and the like; aromatic hydrocarbons such as benzene, toluene and the like; etc.; and it is also possible to use an excess of the amine as the solvent as well as the reactant. The amine of the general formula (VII) includes, for example, mono- or di-$C_{1-8}$alkylamines such as methylamine, ethylamine, n-propylamine, isopropylamine, n-butylamine, tert.-butylamine, n-amylamine, isoamylamine, n-hexylamine, dimethylamine, di-($\beta$-hydroxyethyl)amine, diethylamine, di-n-propylamine, di-n-butylamine and the like; $C_{2-4}$alkenylamines such as allylamine, (3-methyl-2-butenyl)amine and the like; $C_{3-6}$cycloalkylamines such as cyclohexylamine and the like; substituted $C_{1-4}$alkylamines such as (3-acetoxy-n-propyl)amine, 2-chloroethylamine and the like; ar-$C_{1-4}$alkylamines such as benzylamine and the like; and heterocyclic amines such as pyrrolidine, piperidine, morpholine, N-methylpiperazine and the like.

The compound of the general formula (XI) or (XII) or a reactive derivative in the carboxyl group thereof is reacted with an amine of the general formula (V) to obtain a compound of the general formula (XIII) or (XIV), respectively. When the compound of the general formula (XI) or (XII) is subjected to the reaction, it is reacted with the amine of the general formula (V) in the presence of a condensing agent, for example, dicyclohexylcarbodiimide, N,N'-carbonyldiimidazole or Woodward's reagent-K, and when a reactive derivative in the carboxyl group of the compound of the general formula (XI) or (XII) is subjected to the reaction, the conventional reactive derivative such as mixed acid anhydride with a monoalkyl ester of carbonic acid such as ethyl chlorocarbonate or the like; acid azide; or the like is reacted with the amine of the general formula (V) for $\omega$-amidation, whereby a compound of the general formula (XIII) or (XIV) is obtained. In this case, as the amine of the general formula (V), the same amines as described above for the amine of the formula (VII) may be exemplified. When a condensing agent is used in the above-mentioned reaction, reaction conditions of usual amidation may be employed, but in particular, it is preferable to effect the reaction at about $-25°$ C. to 50° C. by using a halogenated hydrocarbon such as methylene chloride or the like as a solvent. Also when the mixed acid anhydride or the acid azide is used in the above-mentioned reaction, the reaction proceeds under substantially the same conditions as described above.

As to removal of the amino-protecting group of the compound of the general formula (XIV) thus obtained, the removal conditions vary depending on the kind of the protecting group used, but the removal can be conducted by a conventional method in all the cases. For example, when the protecting group is a benzyloxycarbonyl group, the removal can easily be conducted by addition of hydrogen bromide in acetic acid or by catalytic reduction, whereby a compound of the general formula (II) can be obtained.

(2) Subsequently, the compound of the general formula (II) or a salt thereof is reacted with a compound of the general formula (III) to obtain an objective compound of the general formula (I) or a salt thereof. In this case, a condensing agent such as dicyclohexylcarbodiimide or the like is used. In place of the compound of the general formula (III), a reactive derivative in the carboxyl group thereof may be subjected to the reaction. The reactive derivative includes, for example, an acid halide (e.g., an acid chloride), a mixed acid anhydride (e.g., a mixed acid anhydride with ethyl chlorocarbonate), an active ester (e.g. an active ester with N-hydroxy succinimide), an acid azide, etc., and when these are subjected to the reaction, reaction conditions of usual amidation are employed.

As the solvent used in the present reaction, there is preferably used any of all solvents which do not adversely affect the reaction, for example, halogenated hydrocarbons such as methylene chloride or the like; ethers such as tetrahydrofuran, dioxane and the like; and nitriles such as acetonitrile and the like. The reaction temperature may be $-25°$ C. to $50°$ C. though it varies depending on the compounds used in this reaction. In particular, it is preferable to effect the reaction at room temperature in the presence of a deacidifing agent such as triethylamine, pyridine or the like when there is used an acid halide which is a reactive derivative in the carboxyl group of a compound of the general formula (III); at room temperature when an active ester is used; at $-25°$ C. to $0°$ C. when a mixed acid anhydride is used; at $-5°$ C. to room temperature when an acid azide is used; and at about $0°$ C. in the presence of a condensing agent when the carboxylic acid is used. The reaction is completed in 5 minutes to 20 hours.

In a series of the reactions in the production process described above, there is obtained an objective compound having the DL configuration when there is used the DL-form of an amino acid of the general formula (IX) as a starting material; an objective compound having the L configuration when the L-form of the amino acid is used; or an objective compound having the D configuration when the D-form of the amino acid is used, respectively.

2. Process for producing the compound of the general formula (IV) or (VIII) and the Production Process [B]

(1) A compound of the general formula (IX) and a reactive derivative in the carboxyl group of a compound of the general formula (III) are subjected to Schotten-Baumann reaction to obtain a compound of the general formula (VIII), which is the heated together with a carboxylic acid anhydride such as acetic anhydride or the like to form an intramolecular anhydride of a compound of the general formula (XV). Thereafter, the anhydride of the general formula (XV) formed is reacted with an amine of the general formula (VII) in water, aqueous acetone or aqueous dioxane, preferably, in water, at $-5°$ C. to $5°$ C. to obtain a compound of the general formula (IV). In this case, a small amount of $\omega$-amides are produced in addition to the $\alpha$-amides but can easily be separated by pH resolution or the like.

(2) Subsequently, the compound of the general formula (IV) or a reactive derivative in the carboxyl group thereof is reacted with an amine of the general formula (V) in the same manner as with the conversion of the compound of the general formula (XI) or (XII) to the compound of the general formula (XIII) or (XIV), respectively, in above 1-(1), whereby a compound of the general formula (I) can be obtained. Here, examples of the reactive derivative in the carboxyl group of the compound of the general formula (IV) include conventional reactive derivatives such as mixed acid anhydrides with a monoalkyl ester of carbonic acid such as ethyl chlorocarbonate or the like; acid azides; and the like. In the production process described above, in some cases, recemization takes place in the step of obtaining the compound of the general formula (IV) from the compound of the general formula (VIII) and the objective compound is obtained as the DL-form.

3. Process for producing the compound of the general formula (VI) and the Production Process [C]

(1) Asparagine, glutamine or 2-amino-5-carbamoylvaleric acid and a reactive derivative in the carboxyl group of a compound of the general formula (III) are subjected to the same Schotten-Baumann reaction as described in above 2-(1), to obtain the compound of the general formula (VI) in which $R^1$ and $R^2$ are hydrogen atoms. The $\alpha$-carboxyl group and the $\alpha$-amino group or aspartic acid, glutamic acid or 2-amino-adipic acid are to be protected with the above-mentioned protecting groups commonly used in this field to obtain the compound of the general formula (VI) in which $R^1$ and $R^2$ are other than hydrogen atoms. Preferable protecting groups include carboxyl-protecting groups and amino-protecting groups which differ from each other in removal conditions, and are, for example, those comprising a combination of a tert.-butyl group and a benzyloxycarbonyl group, a combination of a benzyl group and a tert.-butoxycarbonyl group or the like. Under the protection with these protecting groups, a compound of the general formula (XVI) is obtained, after which a reactive of this compound or a reactive derivative in the carboxyl group thereof with an amine of the general formula (V) is effected under the same conditions as with the amidation in above 1-(1) to obtain a compound of the general formula (XVII). Subsequently, the $\alpha$-carboxyl-protecting group and the $\alpha$-amino-protecting group are removed to obtain a compound of the general formula (XVIII), or the $\alpha$-amino-protecting group alone is removed to obtain a compound of the general formula (XIX). The compound thus obtained and a compound of the general formula (III) or a reactive derivative in the carboxyl group thereof are subjected to acylation under the same conditions as with the acylation in above 2 to obtain a compound of the general formula (VI) or (XX). The compound of the general formula (XX) can be converted into the compound of the general formula (XI) by removing the $\alpha$-carboxyl-protecting group by a conventional method.

(2) The compound of the general formula (VI) thus obtained or a reactive derivative in the carboxyl group thereof and an amine of the general formula (VII) are subjected to amidation under the same conditions as with the amidation in the production process 2, whereby a compound of the general formula (I) can be obtained.

4. Process for producing the compound of the general formula (VIII) and the Production Process [D]

(1) An amino acid of the general formula (IX) is reacted with a compound of the general formula (III) or a reactive derivative in the carboxyl group thereof under the same conditions as described in above 2-(1) to obtain a compound of the general formula (VIII).

(2) The compounds of the general formula (VIII) or a reactive derivative in the carboxyl group thereof is reacted with an amine of the general formula (V) under the same amidation conditions as described in the production process 1, except that the amine of the general formula (V) is used in a proportion of 2 or more moles per mole of the compound of the general formula (VIII) or a reactive derivative in the carboxyl group thereof, to obtain a compound of the general formula (Ia).

In each of the production processes described in above 1, 2, 3 and 4, in conducting the amidation, the amine of the general formula (V) or (VII) can be selected depending upon purposes and converted into an amide.

Next, the pharmacological effects of typical compounds of this invention are explained below.

-continued
Test compound:

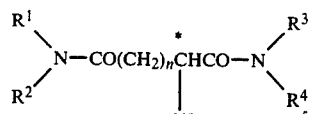

*assymetric carbon atom

TABLE 1

| Test compound No. | $R^1$ | $R^2$ | $R^3$ | $R^4$ | $R^5$ | A | n | Configuration* | $ED_{50}$ values (mg/kg) |
|---|---|---|---|---|---|---|---|---|---|
| 1 | H | —CH$_3$ | —CH$_2$CH$_2$CH$_3$ | —CH$_2$CH$_2$CH$_3$ | furan | —CH=CH— (trans) | 2 | DL | 6.6 |
| 2 | —CH$_3$ | " | " | " | " | —CH=CH— (trans) | " | " | 9 |
| 3 | " | " | —CH$_3$ | —CH$_3$ | " | —CH=CH— (trans) | " | " | 10.8 |
| 4 | " | " | " | " | benzofuran | —CH=CH— (trans) | " | " | 5.9 |
| 5 | " | " | —CH$_2$CH$_2$CH$_3$ | —CH$_2$CH$_2$CH$_3$ | " | —CH=CH— (trans) | " | " | 6.2 |
| 6 | " | " | cyclohexyl | | " | —CH=CH— (trans) | " | " | 6.4 |
| Proglumide | | | | | | | | | 800 |

1. Anti-Ulcer Activity (1) Each compound of this invention or proglumide was orally administrated to Wistar strain rats (♂, body wt. 180–220 g, 8 rats per group) starved for 24 hours, and after 1 hour, Indomethacin (a registered trade mark) was orally administered thereto at a dose of 25 mg/kg. On the other hand, Indomethacin alone was orally administered to a control group at the same dose. After 5 hours, the stomach of each rat was removed, and then the lengths of the ulcers were measured and there were determined doses of the compounds of this invention and proglumide at which the sum total of the lengths is 50% of that measured for the control group ($ED_{50}$ values). The results are shown in Table 1.

Test compound:

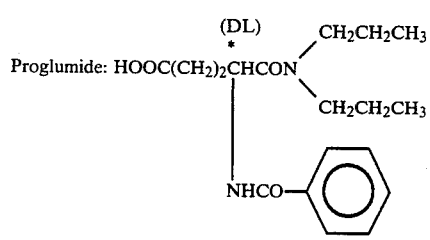

(2) Each compound of this invention or proglumide was intraperitoneally administered to Wistar strain rats (♂, body wt. 180–220 g, 8 rats per group) starved for 24 hours at a dose of 50 mg/kg, and after 1 hour, Indomethacin (a registered trade mark) was orally administered thereto at a dose of 25 mg/kg. On the other hand, Indomethacin alone was orally administered to a control group at the same dose. After 5 hours, the stomach of each rat was removed, and then the sum total of the lengths of the ulcers was measured and compared with that measured for the control group, whereby the inhibition percentage was calculated. The results are shown in Table 2.

Test compound:

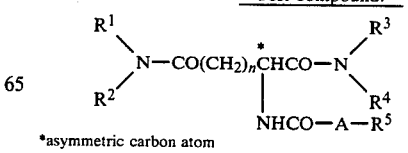

*asymmetric carbon atom

TABLE 2

| Test compound No. | R¹ | R² | R³ | R⁴ | R⁵ | A | n | Configuration* | Inhibition percentage (%) |
|---|---|---|---|---|---|---|---|---|---|
| 7 | —CH₃ | —CH₃ | —CH₂CH₂CH₃ | —CH₂CH₂CH₃ |  | —CH=CH— (trans) | 2 | L | 40 |
| 8 | " | " | " | " | 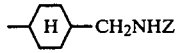 | bond | " | " | 52 |
| 9 | " | " | " | " | 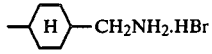 | " | " | " | 59 |
| 10 | " | " | " | " | 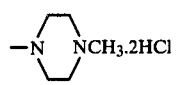 | —CH₂— | " | " | 55 |
| 11 | " | " | " | " | " | —CH₂CH₂— | " | " | 41 |
| 12 | " | " | " | " | " | —CH₂CH₂CH₂— | " | " | 47 |
| 13 | " | " | " | " | 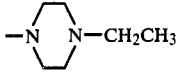 | " | " | " | 55 |
| 14 | " | " | " | " | 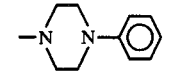 | " | " | " | 52 |
| 15 | " | " | " | " | 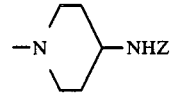 | " | " | " | 51 |
| 16 | " | " | " | " | 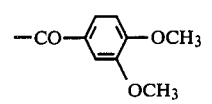 | —CH=CH— (trans) | " | " | 59 |
| 17 | H | —(CH₂)₃CH₃ | H | —(CH₂)₃CH₃ |  | —CH=CH— (trans) | " | DL | 32.1 |
| 18 | " | 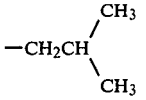 | " | 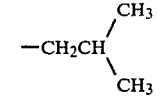 | " | —CH=CH— (trans) | " | " | 37.9 |
| 19 | " | —(CH₂)₃OAc | " | —(CH₂)₃OAc | " | —CH=CH— (trans) | " | " | 53.0 |
| 20 | " | " | " | —CH₂CH₂CH₃ | " | —CH=CH— (trans) | " | " | 53.5 |
| 21 | " | H | " | " | " | —CH=CH— (trans) | " | " | 70.9 |
| 22 | " | —CH₂CH₂Cl | " | —CH₂CH₂Cl | " | —CH=CH— (trans) | " | " | 56.0 |
| 23 | " | 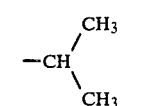 | " | 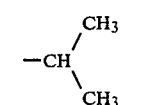 | " | —CH=CH— (trans) | " | " | 52.0 |
| Proglumide | | | | | | | | | 0 |

Z: a benzyloxycarbonyl group
Ac: an acetyl group (3) Each compound of this invention or proglumide was orally administered to Wister strain rats (♂, body wt. 180–220 g, 8 rats per group) starved for 24 hours at a dose of 10 mg/kg and after 30 minutes, 1.5 ml/rat of a 0.2N aqueous sodium hydroxide solution was orally administered thereto. On the other hand, 1.5 ml/rat of a 0.2N aqueous sodium hydroxide solution alone was orally administered to a control group. After 1 hour, the stomach of each rat was removed, and then the sum total of the lengths of the ulcers was measured and compared with that measured for the control group, whereby the inhibition percentage was calculated. The results are shown in Table 3.

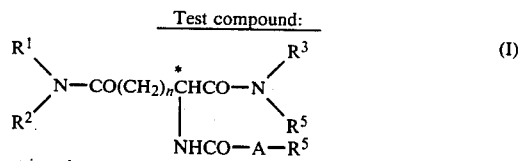

Test compound:

*asymmetric carbon atom
Inhibition percentage:
+: ≧80%
±: 50–79%
−: <50%

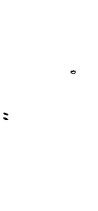

2. Acute toxicity

Each of the compounds of the Test Compound Nos. 2, 3, 4, 5, 6, 17, 23, 30 and 31 was intraperitoneally administered to ddY strain mice (♂, body wt. 23±2 g, 10 mice per group), and the LD$_{50}$ values were measured to find that all of them were 600 mg/kg or more.

As described above, it can be seen that the compound of this invention has a very high anti-ulcer activity as compared with proglumide which is commercially available anti-ulcer agent.

The compound of this invention can be used for curing human and animal ulcers, and can be used therefore in pharmaceutical forms commonly used in this field, for example, capsules, tablets, granules and the like, and in order to prepare them, there may be added various additives, for example, excipients, lubricants, sugars and the like.

When the anti-ulcer agent of this invention is administered to a human being, it is sufficient, in general, to administer it orally to an adult in a dosage of 1 mg to 1,000 mg a day in one to several portions, though the dosage, the administration method, the administration time and the like may properly be selected depending on the symptoms of patients.

Next, Examples and Preparation Examples of the compound of this invention are described below but are not intended to limit this invention.

EXAMPLE 1

Production of

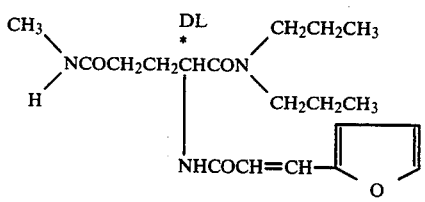

(1) To 1 liter of toluene were added 300 g of DL-N-benzyloxycarbonylglutamic acid, 48 g of paraformaldehyde and 12 g of p-toluenesulfonic acid monohydrate, and azeotropic dehydration was then carried out for 1 hour. After completion of the reaction, the solvent was removed by distillation under reduced pressure, and the oily substance thus obtained was dissolved in 500 ml of ethyl acetate, after which the resulting solution was washed with water and then dried over anhydrous magnesium sulfate, and the solvent was removed by distillation under reduced pressure to obtain oily DL-3-benzyloxycarbonyl-4-(2-carboxyethyl)oxazolidin-5-one.

This product was dissolved in 600 ml of toluene, and 420 g of di(n-propyl)-amine was added, after which azeotropic dehydration was carried out for 2-3 hours. After completion of the reaction, the solvent was removed by distillation under reduced pressure, and 500 ml of ethyl acetate was added to the residue. After the resulting solution was washed with 300 ml of diluted hydrochloric acid, 500 ml of a 10% aqueous sodium hydroxide solution was added, and the resulting mixture was thoroughly shaken, after which the aqueous layer was separated. Subsequently, the aqueous layer was adjusted to pH 6 with diluted hydrochloric acid, and 500 ml of ethyl acetate was added, after which the resulting mixture was thoroughly shaken, and then the organic layer was separated. After the organic layer separated was dried over anhydrous magnesium sulfate, the solvent was removed by distillation under reduced pressure to obtain 272 g (yield 70%) of DL-N$^2$-benzyloxycarbonyl-N$^1$,N$^1$-di-n-propyl-α-glutamylamide having a melting point of 108°-110° C.

(2) In 500 ml of methylene chloride was dissolved 36.4 g of the DL-N$^2$-benzyloxycarbonyl-N$^1$,N$^1$-di-n-propyl-α-glutamylamide, and 25.2 g of triethylamine and 12 g of ethyl chlorocarbonate were added dropwise at −20° C. to −15° C., after which the resulting mixture was stirred at the same temperature for 30 minutes, and then 7.4 g of methylamine hydrochloride was added in portions. Subsequently, the resulting mixture was stirred at the same temperature for 2 hours, after which the reaction mixture was washed successively with 100 ml of diluted hydrochloric acid, 100 ml of a 5% aqueous sodium hydroxide solution and 100 ml of water, and then dried over anhydrous magnesium sulfate. And, the solvent was removed by distillation under reduced pressure to obtain 35.8 g (yield 95%) of DL-2-benzyloxycarbonylamino-N$^5$-methyl-N$^1$,N$^1$-di(n-propyl)-pentane-1,5-diamide having a melting point of 75°-76° C.

(3) In 50 ml of isopropanol was dissolved 9.3 g of DL-2-benzyloxycarbonylamino-N$^5$-methyl-N$^1$,N$^1$-di(n-propyl)pentane-1,5-diamide, after which 2.2 ml of conc. hydrochloric acid and 0.5 g of 10% palladium-carbon were added and catalytic reduction was carried out at room temperature under atmospheric pressure. After completion of the reaction, the palladium-carbon was removed by filtration and the solvent was removed by distillation under reduced pressure to obtain 6.7 g (yield 97%) of DL-2-amino-N$^5$-methyl-N$^1$,N$^1$-di(n-propyl)-pentane-1,5-diamide hydrochloride having a melting point of 125°-127° C.

(4) In 75 ml of methylene chloride was dissolved 1.5 g of β-(2-furyl)acrylic acid, and 2.7 g of triethylamine and 1.3 g of ethyl chlorocarbonate were successively added thereto dropwise at −25° C. to −20° C. After 30 minutes, 3 g of the DL-2-amino-N$^5$-methyl-N$^1$,N$^1$-di(n-propyl)-pentane-1,5-diamide hydrochloride was added to the above solution, and the resulting mixture was subjected to reaction at the same temperature for 30 minutes and at room temperature for 30 minutes. After completion of the reaction, the reaction mixture was washed successively with 30 ml of a 5% aqueous sodium hydroxide solution, 30 ml of diluted hydrochloric acid and 30 ml of water and then dried over anhydrous magnesium sulfate, and the solvent was removed by distillation under reduced pressure to obtain 3.1 g (yield 80%) of DL-2-[β-(2-furyl)acrylamido]-N$^5$-methyl-N$^1$,N$^1$-di(n-propyl)pentane-1,5-diamide having a melting point of 112°-113° C.

| Elementary analysis values ($C_{19}H_{29}N_3O_4$) | | | |
|---|---|---|---|
| | C (%) | H (%) | N (%) |
| Calculated | 62.78 | 8.04 | 11.56 |
| Found | 62.85 | 8.23 | 11.62 |

NMR (CDCl$_3$) δ values: 0.85 (3H, t, —CH$_3$), 0.97 (3H, t, —CH$_3$), 1.25-2.60 (8H, m, >CH$_2$×4), 2.87 (3H, d, —CH$_3$), 3.05-3.90 (4H, m, >CH$_2$×2), 5.15 (1H, m, →CH), 6.45-6.67 (2H, m, furan ring H×2), 6.66 (1H, d, —CH=), 7.05-7.45 (1H, m, >NH), 7.54 (1H, d, —CH=), 7.57 (1H, s, furan ring H), 7.83 (1H, d, >NH)

IR (KBr) cm$^{-1}$: ν$_{NH}$ 3300, ν$_{C=O}$ 1635, 1615.

EXAMPLE 2

Production of

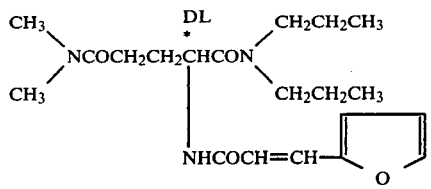

In 75 ml of methylene chloride was dissolved 1.7 g of β-(2-furyl)acrylic acid, and 3 g of triethylamine and 1.5 g of ethyl chlorocarbonate were successively added dropwise at −25° C. to −20° C., followed by adding thereto 4 g of DL-2-amino-$N^5$,$N^5$-dimethyl-$N^1$,$N^1$-di(n-propyl)-pentane-1,5-diamide hydrochloride obtained in substantially the same manner as in Example 1 (1) to (3). The resulting mixture was subjected to reaction at the same temperature for 30 minutes and at room temperature for 30 minutes. Subsequently, after-treatment was carried out in the same manner as in Example 1 (4) to obtain 3.5 g (yield 76%) of DL-2-[β-(2-furyl)acrylamido]-$N^5$,$N^5$-dimethyl-$N^1$,$N^1$-di(n-propyl)-pentane-1,5-diamide having a melting point of 114°–116° C.

| Elementary analysis values ($C_{20}H_{31}N_3O_4$) | | | |
|---|---|---|---|
| | C (%) | H (%) | N (%) |
| Calculated | 63.63 | 8.28 | 11.13 |
| Found | 63.43 | 8.38 | 11.08 |

NMR (CDCl$_3$) δ values: 0.85 (3H, t, —CH$_3$), 0.99 (3H, t, —CH$_3$), 1.25–2.70 (8H, m, >CH$_2$×4), 2.95 (6H, s, —CH$_3$×2), 3.10–4.95 (4H, m, >CH$_2$×2), 5.19 (1H, m, →CH), 6.41–6.57 (2H, m, furan ring H×2), 6.62 (1H, d, —CH═), 7.46 (1H, d, —CH═), 7.48 (1H, s, furan ring H), 8.07 (1H, d, >NH)

IR (KBr) cm$^{-1}$: $\nu_{NH}$ 3370, $\nu_{C═O}$ 1665, 1645, 1610.

EXAMPLE 3

Production of

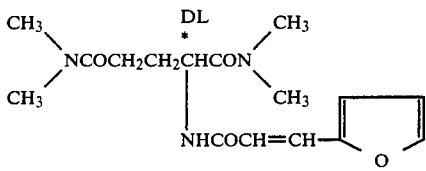

(1) In 75 ml of water was suspended 6.5 g of DL-glutamic acid, and 5.2 g of sodium hydroxide was added, after which the resulting mixture was cooled to −10° C. to −7° C., and a solution of 6 g of β-(2-furyl)acrylic acid chloride in 75 ml of diethyl ether was added thereto dropwise over a period of 1 hour. After the addition, the mixture thus obtained was subjected to reaction at the same temperature for 5 hours, after which the aqueous layer was separated and then adjusted to pH 5.5 with diluted hydrochloric acid. The aqueous layer was washed with two 50-ml portions of ethyl acetate, and the aqueous layer was separated. This aqueous layer was adjusted to pH 2 with diluted hydrochloric acid and then extracted with 100 ml of ethyl acetate, and the organic layer was separated. The organic layer was dried over anhydrous magnesium sulfate, and the solvent was removed by distillation under reduced pressure to obtain 5.5 g (yield 52%) of DL-N-[β-(2-furyl)acryloyl]glutamic acid having a melting point of 174.5°–175.5° C.

(2) In 100 ml of methylene chloride was suspended 5 g of the DL-N-[β-(2-furyl)acryloyl]glutamic acid, and 7 g of triethylamine was added to dissolve it. Subsequently, the resulting solution was cooled to −20° C. to −15° C., after which 4.6 g of ethyl chlorocarbonate was added dropwise, and the resulting mixture was subjected to reaction for 30 minutes. Thereafter, 3.1 g of dimethylamine hydrochloride was added, and the resulting mixture was subjected to reaction at the same temperature for 2 hours. After completion of the reaction, the reaction mixture was washed successively with 50 ml of a 5% aqueous sodium hydroxide solution, 50 ml of diluted hydrochloric acid and 50 ml of water, and dried over anhydrous magnesium sulfate, after which the solvent was removed by distillation under reduced pressure to obtain 3.5 g (yield 55%) of DL-2-[β-(2-furyl)acrylamido]-$N^1$,$N^1$,$N^5$,$N^5$-tetramethyl-pentane-1,5-diamide having a melting point of 178°–180° C.

| Elementary analysis values ($C_{16}H_{23}N_3O_4$) | | | |
|---|---|---|---|
| | C (%) | H (%) | N (%) |
| Calculated | 59.79 | 7.21 | 13.08 |
| Found | 59.93 | 7.32 | 13.09 |

NMR (CDCl$_3$) δ values: 1.5–2.7 (4H, m, >CH$_2$×2), 2.93 (6H, s, —CH$_3$×2), 3.00 (3H, s, —CH$_3$), 3.24 (3H, s, —CH$_3$), 5.16 (1H, m, →CH), 6.34–6.52 (2H, m, furan ring H×2), 6.55 (1H, d, —CH═), 7.34 (1H, d, —CH═), 7.41 (1H, s, furan ring H), 7.74 (1H, d, >NH)

IR (KBr) cm$^{-1}$: $\nu_{NH}$ 3310, $\nu_{C═O}$ 1660, 1640, 1615.

EXAMPLE 4

Production of

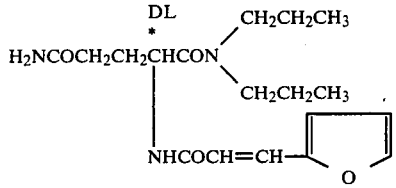

(1) In a mixed solution of 45 ml of a 1N aqueous sodium hydroxide solution and 50 ml of diethyl ether was dissolved 6.5 g of L-glutamine, and a solution of 9 g of β-(2-furyl)acrylic acid chloride in 25 ml of diethyl ether and 60 ml of a 1N aqueous sodium hydroxide solution were added dropwise at the same time with vigorous stirring at −15° C. to −10° C. over a period of 1 hour. After the addition, the resulting mixture was subjected to reaction at 10° C. to 15° C. for 1 hour, and the aqueous layer was separated. The aqueous layer was adjusted to pH 5.5 with 6N hydrochloric acid, washed with three-50 ml portions of ethyl acetate, thereafter adjusted to pH 4.5 with 6N hydrochloric acid, and then washed with 50 ml of ethyl acetate. Subsequently, the solution thus obtained was adjusted to pH 2 with 6N hydrochloric acid, and extracted with two 50-ml portions of ethyl acetate. After the organic layer thus obtained was dried over anhydrous magnesium sulfate, the solvent was removed by distillation under reduced pressure to obtain 1.2 g (yield 10%) of L-$N^2$-[β-(2-furyl)acryloyl]glutamine having a melting point of 163°–164° C.

(2) In a mixed solution of 27.5 ml of anhydrous methylene chloride and 0.69 ml of triethylamine was dissolved 1.1 g of the L-$N^2$-[β-(2-furyl)acryloyl]glutamine, and 0.44 ml of ethyl chlorocarbonate was added at −20° C. to −15° C. The resulting mixture was subjected to reaction at the same temperature for 1 hour, after which 0.68 ml of di(n-propyl)-amine was added, and the mixture thus obtained was subjected to reaction at the same temperature for 1 hour and then at room temperature for 2 hours. After completion of the reaction, the reaction mixture was washed successively with 10 ml of water, 10 ml of 0.5N hydrochloric acid, 10 ml of a saturated aqueous sodium hydrogencarbonate solution and 10 ml of a saturated aqueous sodium chloride solution and dried over anhydrous magnesium sulfate, after which the solvent was removed by distillation under reduced pressure to obtain 0.25 g (yield 17%) of DL-2-[β-(2-furyl)acrylamido]-$N^1$,$N^1$-di(n-propyl)-pentane-1,5-diamide having a melting point of 152.5°–153° C.

NMR (CDCl$_3$) δ values: 0.86 (3H, t, —CH$_3$), 0.93 (3H, t, —CH$_3$), 1.20–2.65 (8H, m, >CH$_2$×4), 2.65–3.85 (4H, m, >CH$_2$×2), 5.20 (1H, m, →CH), 6.45–6.75 (2H, m, furan ring H×2), 6.69 (1H, d, —CH═), 7.07 (2H, bs, —NH$_2$), 7.55 (1H, d, —CH═), 7.58 (1H, s, furan ring H), 8.11 (1H, d, >NH)

IR (KBr) cm$^{-1}$: $\nu_{NH}$ 3400, 3260, 3190, $\nu_{C=O}$ 1670, 1630.

EXAMPLE 5

Production of

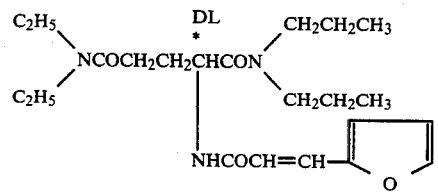

(1) In 20 ml of acetic anhydride was dissolved 5 g of DL-N-[β-(2-furyl)acryloyl]glutamic acid, and the resulting solution was heated at 100° C. for 15 minutes, after which the excessive acetic anhydride was removed by distillation under reduced pressure to obtain DL-N-[β-(2-furyl)acryloyl]glutamic acid anhydride. This product was added to a mixed solution of 5 ml of di(n-propyl)-amine and 5 ml of water with ice-cooling, and the resulting mixture was subjected to reaction for 2 hours. After completion of the reaction, the reaction mixture was adjusted to pH 4 with diluted hydrochloric acid and extracted with two 20-ml portions of ethyl acetate, and the organic layers were combined and then dried over anhydrous magnesium sulfate. Subsequently, the solvent was removed by distillation under reduced pressure to obtain 4 g (yield 62%) of DL-$N^2$-[β-(2-furyl)acryloyl]-$N^1$,$N^1$-di-n-propyl-α-glutamylamide having a melting point of 130°–131° C.

(2) In 100 ml of methylene chloride was dissolved 4 g of the DL-$N^2$-[β-(2-furyl)-acryloyl]-$N^1$,$N^1$-di-n-propyl-α-glutamylamide, after which 1.3 g of triethylamine and 1.4 g of ethyl chlorocarbonate were successively added thereto dropwise at −25° C. to −20° C., and the resulting mixture was subjected to reaction for 30 minutes. Thereafter, 1 g of diethylamine was added dropwise at the same temperature, and the mixture thus obtained was subjected to reaction for 1 hour. Subsequently, after-treatment was carried out in the same manner as in Example 1-(4) to obtain 3.2 g (yield 70%) of DL-2-[β-(2-furyl)acrylamido]-$N^5$,$N^5$-diethhl-$N^1$,$N^1$-di(n-propyl)-pentane-1,5-diamide having a melting point of 117°–117.5° C.

| Elementary analysis values (C$_{22}$H$_{35}$N$_3$O$_4$) | | | |
|---|---|---|---|
| | C (%) | H (%) | N (%) |
| Calculated | 65.16 | 8.70 | 10.36 |
| Found | 65.45 | 8.85 | 10.42 |

NMR (CDCl$_3$) δ values: 0.60–1.40 (12H, m, —CH$_3$×4), 1.40–2.70 (8H, m, >CH$_2$×4), 2.70–4.40 (8H, m, >CH$_2$33 4), 5.20 (1H, m, →CH), 6.52–6.65 (2H, m, furan ring H×2), 6.59 (1H, d, —CH═), 7.52 (1H, d, —CH═), 7.57 (1H, s, furan ring H), 7.65 (1H, d, >NH)

IR (KBr) cm$^{-1}$: $\nu_{NH}$ 3250, $\nu_{C=O}$ 1625.

EXAMPLE 6

Production of

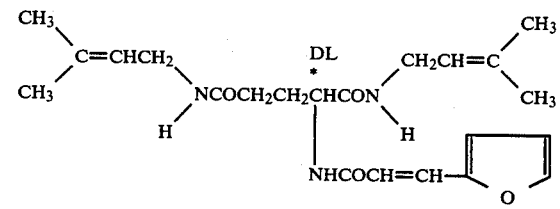

(1) In 1 liter of methylene chloride was suspended 65 g of β-(2-furyl)acrylic acid, and 105 g of triethylamine and 56 g of ethyl chlorocarbonate were successively added thereto dropwise at −15° C. to −10° C., after which the resulting mixture was subjected to reaction at 10° C. to 15° C. for 30 minutes and at room temperature for 30 minutes. Thereafter, 100 g of dimethyl DL-glutamate hydrochloride was added in portions. At the same temperature, the resulting mixture was stirred for 1 hour and thereafter further stirred at room temperature for 3 hours. Subsequently, the reaction mixture was washed successively with 300 ml of diluted hydrochloric acid, 300 ml of a 5% aqueous sodium hydroxide solution and 300 ml of water, and then dried over anhydrous magnesium sulfate, after which the solvent was removed by distillation under reduced pressure to obtain 100 g (yield 81%) of dimethyl DL-N-[β-(2-furyl)acryloyl]glutamate having a melting point of 93°–96° C.

(2) To a mixture of 400 ml of water, 80 ml of methanol and 45 g of sodium hydroxide was added 100 g of the dimethyl DL-N-[β-(2-furyl)acryloyl]glutamate, and the resulting mixture was heated at 60° C. to 65° C. for 4 hours to hydrolyze the ester. The reaction mixture was cooled to room temperature and acidified with hydrochloric acid, and thereafter the precipitated crystals were collected by filtration to obtain 80 g (yield 90%) of DL-N-[β-(2-furyl)acryloyl]glutamic acid having a melting point of 166°–170° C.

(3) In 300 ml of methylene chloride was dissolved 5 g of the DL-N-[β-(2-furyl)acryloyl]glutamic acid, and thereto were successively added 5.4 g of N-hydroxysuccinimide, 5 g of (3-methyl-2-butenyl)amine hydrochloride, 5 g of triethylamine and 9.6 g of dicyclohexylcarbodiimide at room temperature, and the resulting mixture was stirred for 6 hours. Subsequently, the precipitated dicyclohexylurea was removed by filtration, and the filtrate thus obtained was washed successively with 100 ml of diluted hydrochloric acid, 100 ml of a 5% aqueous sodium hydroxide solution and 100 ml of water, and then dried over anhydrous magnesium sulfate, after which the solvent was removed by distillation under reduced pressure to obtain 4 g (yield 51%) of DL-2-[β-(2-furyl)acrylamido]-N$^1$,N$^5$-bis(3-methyl-2-butenyl)pentane-1,5-diamide having a melting point of 199°–203° C.

IR (KBr) cm$^{-1}$: $\nu_{NH}$ 3290, $\nu_{C=O}$ 1650–1600.

EXAMPLE 7

Production of

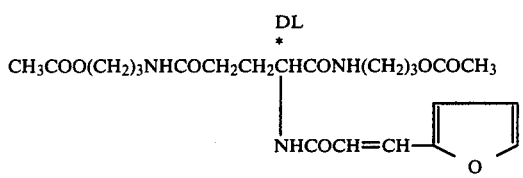

(1) In 300 ml of methylene chloride was dissolved 50 g of 3-aminopropanol, and thereto were successively added dropwise 33 g of triethylamine and 57 g of benzyloxycarbonyl chloride at −10° C. to −5° C. At the same temperature, the resulting mixture was stirred for 1 hour and then further stirred at room temperature for 1 hour. Subsequently, the reaction mixture was washed successively with 100 ml of diluted hydrochloric acid and 100 ml of water, and thereafter dried over anhydrous magnesium sulfate, after which the solvent was removed by distillation under reduced pressure to obtain 60 g (yield 86%) of 3-(benzyloxycarbonylamino)-propanol having a melting point of 55°–56° C.

(2) In 200 ml of methylene chloride was dissolved 21 g of the 3-(benzyloxycarbonylamino)propanol, and 11 g of triethylamine was added thereto, after which 8.6 g of acetyl chloride was added thereto dropwise at −10° C. to −5° C. The resulting mixture was subjected to reaction at the same temperature for 1 hour. Subsequently, at room temperature, the reaction mixture was washed successively with 50 ml of diluted hydrochloric acid, 50 ml of a saturated aqueous sodium hydrogencarbonate solution and 50 ml of water, and then dried over anhydrous magnesium sulfate, after which the solvent was removed by distillation under reduced pressure to obtain 28 g of oily 1-acetoxy-3-(benzyloxycarbonylamino)propane.

(3) In 200 ml of isopropanol was dissolved 28 g of the 1-acetoxy-3-(benzyloxycarbonylamino)propane, and 2.5 g of 5% palladium-carbon and 10 ml of conc. hydrochloric acid were added thereto, after which the resulting mixture was subjected to catalytic reduction at room temperature. Subsequently, the palladium-carbon was removed by filtration and the solvent was removed by distillation under reduced pressure to obtain 12 g of oily 1-acetoxy-3-aminopropane hydrochloride.

(4) In 200 ml of methylene chloride was dissolved 1.5 g of DL-N-[β-(2-furyl)acryloyl]glutamic acid, and 2 g of the 1-acetoxy-3-aminopropane hydrochloride, 1.5 g of N-hydroxysuccinimide and 3.2 g of dicyclohexylcarbodiimide were successively added thereto, after which the resulting mixture was subjected to reaction at room temperature for 2 hours. Subsequently, the reaction mixture was treated in the same manner as in Example 6-(3) to obtain 2 g (yield 36%) of DL-N$^1$,N$^5$-bis(3-acetoxypropyl)-2-[β-(2-furyl)acrylamido]pentane-1,5-diamide having a melting point of 132°–134° C.

IR (KBr) cm$^{-1}$: $\nu_{NH}$ 3280, $\nu_{C=O}$ 1730, 1630, 1610.

EXAMPLE 8

Production of

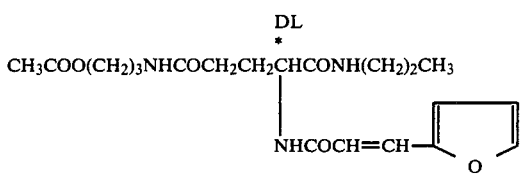

(1) To 300 ml of toluene were added 100 g of DL-N-benzyloxycarbonylglutamic acid, 20 g of powdery paraformaldehyde and 4 g of p-toluenesulfonic acid monohydrate, and the resulting mixture was subjected to azeotropic dehydration for 3 hours. Subsequently, the solvent was removed by distillation under reduced pressure, and the oily product thus obtained was dissolved in 200 ml of ethyl acetate, after which the resulting solution was washed with water. The organic layer thus formed was then separated and dried over anhydrous magnesium sulfate, and the solvent was removed by distillation under reduced pressure to obtain oily DL-3-benzyloxycarbonyl-4-(2-carboxyethyl)oxazolidin-5-one. Thus product was dissolved in 250 ml of toluene with heating, and 120 g of n-propylamine was added thereto, after which the resulting mixture was heated under reflux for 3.5 hours. Subsequently, the solvent was removed by distillation under reduced pressure, and the resulting residue was dissolved in 250 ml of ethyl acetate, after which the resulting solution was washed with three 100-ml portions of diluted hydrochloric acid. The resulting organic layer was separated, and the pH thereof was adjusted to 10 with a 3% aqueous sodium hydroxide solution, after which the resulting aqueous layer was separated. The pH of the aqueous layer was adjusted to 6 with diluted hydrochloric acid, and the crystals thus precipitated were collected by filtration to obtain 87 g (yield 76%) of DL-N$^2$-benzyloxycarbonyl-N$^1$-n-propyl-α-glutamylamide having a melting point of 132°–135° C.

(2) In 500 ml of methylene chloride was dissolved 14 g of the DL-N$^2$-benzyloxycarbonyl-N$^1$-n-propyl-α-glutamylamide, and thereto were added dropwise 13.1 ml of triethylamine and triethylamine and 4.9 g of ethyl chlorocarbonate at −20° C. to −10° C., after which the resulting mixture was stirred for 30 minutes. To the mixture was added 7.5 g of the 1-acetoxy-3-aminopropane hydrochloride prepared in Example 7-(3) in portions. Subsequently, at the same temperature, the resulting mixture was stirred for 1 hour, and then further stirred at room temperature for 1 hour. The reaction mixture thus obtained was poured into 500 ml of water, and the resulting organic layer was separated. This organic layer was washed successively with 200 ml of diluted hydrochloric acid and 200 ml of a saturated aqueous sodium hydrogencarbonate solution and dried over anhydrous magnesium sulfate, and the solvent was removed by distillation under reduced pressure to obtain 14.6 g (yield 81%) of DL-N$^5$-(3-acetoxypropyl)-2-(benzyloxycarbonylamino)-N$^1$-n-propylpentane-1,5-diamide having a melting point of 98°–102° C.

(3) In 200 ml of methanol was dissolved 14.6 g of the DL-N⁵-(3-acetoxypropyl)-2-(benzyloxycarbonylamino)-N¹-n-propylpentane-1,5-diamide, and thereto were added 1.5 g of 5% palladium-carbon and 8 ml of conc. hydrochloric acid, after which the resulting mixture was subjected to catalytic reduction at room temperature. Subsequently, the palladium-carbon was removed by filtration and the solvent was removed by distillation under reduced pressure to obtain oily DL-N⁵-(3-acetoxypropyl)-2-amino-N¹-n-propylpentane-1,5-diamide hydrochloride. This product was dissolved in 50 ml of methylene chloride, and the resulting solution was added dropwise at −20° C. to −10° C. to the mixed acid anhydride in methylene chloride separately prepared in the same manner as in Example 8-(2) from 4.3 g of β-(2-furyl)acrylic acid, 10 ml of triethylamine and 3.7 g of ethyl chlorocarbonate, after which the resulting mixture was stirred at the same temperature for 30 minutes. Subsequently, the mixture was further stirred at room temperature for 30 minutes, and washed successively with 50 ml of diluted hydrochloric acid, 50 ml of a saturated aqueous sodium hydrogencarbonate solution and 50 ml of water, and thereafter dried over anhydrous magnesium sulfate. The solvent was then removed by distillation under reduced pressure to obtain 4.2 g (yield 24%) of DL-N⁵-(3-acetoxypropyl)-2-[β-(2-furyl)acrylamido]-N¹-n-propylpentane-1,5-diamide having a melting point of 154°–156° C.

IR (KBr) cm⁻¹: $\nu_{NH}$ 3280, $\nu_{C=O}$ 1730, 1630, 1610.

EXAMPLE 9

The compounds shown in Table 4 were obtained by the same production processes [A] to [D] as practised in Examples 1 to 8.

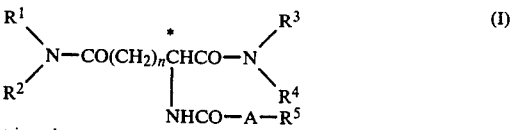

$$\begin{array}{c} R^1 \\ \diagdown \\ R^2 \end{array} N-CO(CH_2)_n \overset{*}{C}HCO-N \begin{array}{c} R^3 \\ \diagup \\ R^4 \end{array} \qquad (I)$$
$$\hspace{3cm} | \\ \hspace{3cm} NHCO-A-R^5$$

*asymmetric carbon atom

Note

Me: a methyl group, Et: an ethyl group, n-Pr: a n-propyl group, i-Pr: an isopropyl group, n-Bu: a n-butyl group, i-Bu: an isobutyl group, t-Bu: A tert.-butyl group, n-Am: a n-amyl group, i-Am: an isoamyl group, n-Hex: a n-hexyl group, Ph: a phenyl group, Z: a benzyloxycarbonyl group, ⁀: a methylene group ⁀⁀: an ethylene group, ⁀⁀⁀: a trimethylene group, ⁀⁀⁀⁀: a tetramethylene group, ⁀⁀: an allyl group.

TABLE 4

| | | | | Symbol in General Formula (I) | | | | Melting point (°C.) | IR (cm⁻¹) | Remarks |
|---|---|---|---|---|---|---|---|---|---|---|
| $R^1$ | $R^2$ | $R^3$ | $R^4$ | $R^5$ | A | n | Configuration* | | | |
| Me | Me | n-Pr | n-Pr | -CO-⟨phenyl⟩-OMe | ⟨CH⟩ | 2 | L | 121–123 | $\nu_{NH}$ 3400<br>$\nu_{C=O}$ 1635 | *1 |
| " | " | " | " | -CO-⟨phenyl⟩(OMe)(OMe) | -CHCH₂-<br>\|<br>OH | " | " | — | $\nu_{NH}$ 3400<br>$\nu_{C=O}$ 1610 | *1 |
| " | " | " | " | ⟨pyridyl⟩ | Bond | " | " | 108–110 | $\nu_{NH}$ 3305<br>$\nu_{C=O}$ 1640, 1620 | *1 |
| " | " | " | " | ⟨N-Et dioxopiperazinyl⟩ | " | " | " | 56–58 | $\nu_{NH}$ 3300<br>$\nu_{C=O}$ 1718, 1685, 1637 | *1 |
| " | " | " | " | ⟨furanyl⟩ | " | " | " | — | $\nu_{NH}$ 3400, 3270<br>$\nu_{C=O}$ 1635 | *1 |
| " | " | " | " | ⟨pyranone⟩ | " | " | " | 132–134 | $\nu_{C=O}$ 1730, 1680 | *1 |
| " | " | " | " | ⟨thienyl⟩ | " | " | " | 90–92 | $\nu_{NH}$ 3320<br>$\nu_{C=O}$ 1620 | *1 |
| " | " | " | " | ⟨Me-thiazolyl⟩ | " | " | " | 78–80 | $\nu_{NH}$ 3260<br>$\nu_{C=O}$ 1635 | *1 |

TABLE 4-continued

| R¹ | R² | R³ | R⁴ | R⁵ | A | n | Configuration* | Melting point (°C) | IR (cm⁻¹) | Remarks |
|---|---|---|---|---|---|---|---|---|---|---|
| " | " | " | " | 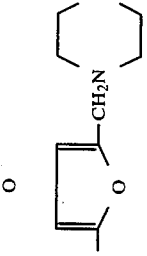 | " | " | " | Amorphous | $\nu_{NH}$ 3400 $\nu_{C=O}$ 1620 | *1 |
| " | " | " | " | 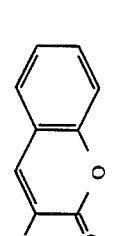 | " | " | " | Amorphous | $\nu_{NH}$ 3260 $\nu_{C=O}$ 1635 | *1 |
| " | " | " | " | 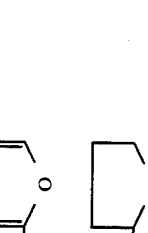 | " | " | " | 124–126 | $\nu_{NH}$ 3330 $\nu_{C=O}$ 1710, 1610 | *1 |
| " | " | " | " | 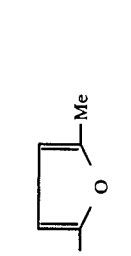 | " | " | " | — | $\nu_{NH}$ 3300 $\nu_{C=O}$ 1620 | *1 |
| " | " | " | " | 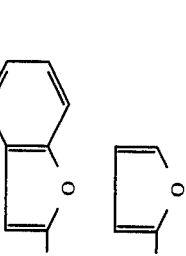 | " | " | " | — | $\nu_{NH}$ 3300 $\nu_{C=O}$ 1620 | *1 |
| " | " | " | " |  | —CH=CH— (trans) | " | " | — | $\nu_{NH}$ 3290 $\nu_{C=O}$ 1620 | *1 |
| " | " | " | " | 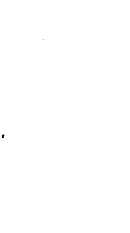 | —CH=CH— (trans) | " | " | — | $\nu_{NH}$ 3270 $\nu_{C=O}$ 1660, 1640, 1620 | *1 |
| " | " | " | " | 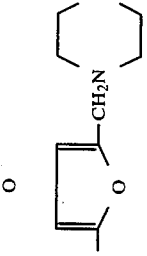 | —C=CH— \| Me (trans) | " | " | — | $\nu_{NH}$ 3350 $\nu_{C=O}$ 1630 | *1 |
| " | " | " | " | 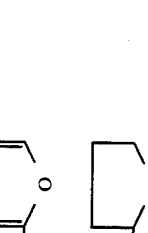 | —C=CH— \| Ph (trans) | " | " | — | $\nu_{NH}$ 3400 $\nu_{C=O}$ 1630 | *1 |
| " | " | " | " | " | —CH=CHCH=CH— | " | " | — | $\nu_{NH}$ 3250 | *1 |

TABLE 4-continued

| R¹ | R² | R³ | R⁴ | R⁵ | A | n | Configuration* | Melting point (°C.) | IR (cm⁻¹) | Remarks |
|---|---|---|---|---|---|---|---|---|---|---|
| | | | | | (trans,trans) | | | | $\nu_{C=O}$ 1605 | |
| " | " | " | " | ![thiophene] | —CH=CH— (trans) | " | " | 135–137 | $\nu_{NH}$ 3250 $\nu_{C=O}$ 1630, 1610 | *1 |
| " | " | " | " | ![pyridine] | —CH=CH— (trans) | " | " | 82–84 | $\nu_{NH}$ 3260 $\nu_{N=}$ 1635 | *1 |
| " | " | " | " | ![3,4-dimethoxybenzoyl -CO-C₆H₃(OMe)₂] | —CH=CH— (trans) | " | " | — | $\nu_{NH}$ 3270 $\nu_{C=O}$ 1620 | *1 |
| " | " | " | " | ![4-methylpiperazinocarbonyl -CO-N(CH₂CH₂)₂NMe] | —CH=CH— (trans) | " | " | 96–101 | $\nu_{NH}$ 3240 $\nu_{C=O}$ 1620 | *1 |
| " | " | " | " | ![-CO-furan] | —CH=CH— (trans) | " | " | — | $\nu_{NH}$ 3280 $\nu_{C=O}$ 1660–1620 | *1 |
| " | " | " | " | —COMe | —CH=CH— (trans) | " | " | — | $\nu_{NH}$ 3270 $\nu_{C=O}$ 1630 | *1 |
| " | " | Me | Me | ![cyclohexyl] | —CH=CH— (trans) | " | DL | 209–210 | $\nu_{NH}$ 3290 $\nu_{C=O}$ 1610 | *2 |
| " | " | | | ![2-methylbenzofuran] | —CH=CH— (trans) | " | " | 145–146.5 | $\nu_{NH}$ 3300 $\nu_{C=O}$ 1610 | *1 |

TABLE 4-continued
| R¹ | R² | R³ | R⁴ | R⁵ | A | Configuration* | Melting point (°C.) | IR (cm⁻¹) | Remarks |
|---|---|---|---|---|---|---|---|---|---|
| " | " | |  |  | —CH=CH— (trans) | " | 160–162 | $\nu_{NH}$ 3250 $\nu_{C=O}$ 1670, 1640, 1600 | *1 |
| " | " | n-Pr | n-Pr | —CO—Ph | —CH=CH— (trans) | L | — | $\nu_{NH}$ 3300 $\nu_{C=O}$ 1740, 1680, 1630 | *1 |
| " | " | " | " |  | Bond | " | >280 | $\nu_{NH}$ 3500, $\nu_{C=O}$ 1640 | *1 |
| " | " | " | " | " |  | " | Amorphous | $\nu_{NH}$ 3400–3200 $\nu_{C=O}$ 1680, 1640 | *1 |
| " | " | " | " |  |  | " | — | $\nu_{NH}$ 3300 $\nu_{C=O}$ 1620 | *1 |
| " | " | " | " | " |  | " | — | $\nu_{NH}$ 3300 $\nu_{C=O}$ 1630 | *1 |
| " | " | " | " | " |  | " | — | $\nu_{NH}$ 3360–3280 $\nu_{C=O}$ 1630 | *1 |
| " | " | " | " |  | " | " | — | $\nu_{NH}$ 3290 $\nu_{C=O}$ 1635 | *1 |
| " | " | " | " |  | " | " | — | $\nu_{NH}$ 3290 $\nu_{C=O}$ 1630 | *1 |

TABLE 4-continued

| R¹ | R² | R³ | R⁴ | R⁵ | A | n | Configuration* | Melting point (°C.) | IR (cm⁻¹) | Remarks |
|---|---|---|---|---|---|---|---|---|---|---|
| " | " | " | " | −N⟨⟩N−n-Bu | " | " | " | — | $\nu_{NH}$ 3300 $\nu_{C=O}$ 1640 | *1 |
| " | " | " | " | −N⟨⟩N−Ph | " | " | " | — | $\nu_{NH}$ 3290 $\nu_{C=O}$ 1630 | *1 |
| " | " | " | " | −N⟨⟩N−CH₂−Ph | " | " | " | — | $\nu_{NH}$ 3250 C=O 1710, 1600 | *1 |
| " | " | " | " | −N⟨⟩N−CH₂−(3,4,5-(OMe)₃C₆H₂) | " | " | " | — | $\nu_{NH}$ 3290 $\nu_{C=O}$ 1620 | *1 |
| " | " | " | " | −N⟨⟩N−CH₂CH₂−OH | ⟨ | " | " | — | $\nu_{NH}$ 3500−3200 $\nu_{C=O}$ 1620 | *1 |
| " | " | " | " | −N⟨⟩N−CH₂−(3,4,5-(OMe)₃C₆H₂) | " | " | " | Amorphous | $\nu_{NH}$ 3350 $\nu_{C=O}$ 1630 | *1 |
| " | " | " | " | −N⟨⟩N−CH₂−(2,3-(OMe)₂C₆H₃) | " | " | " | " | $\nu_{NH}$ 3500−3350 $\nu_{C=O}$ 1640 | *1 |

TABLE 4-continued
| R¹ | R² | R³ | R⁴ | R⁵ | A | n | Configuration* | Melting point (°C.) | IR (cm⁻¹) | Remarks |
|---|---|---|---|---|---|---|---|---|---|---|
| " | " | " | " | 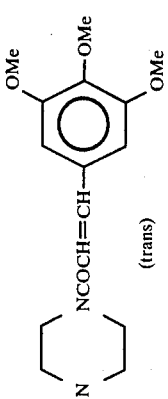 | " | " | " | " | $\nu_{NH}$ 3470–3340 $\nu_{C=O}$ 1610 | *1 |
| " | " | " | " | 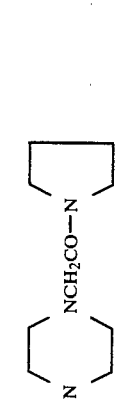 | " | " | " | " | $\nu_{NH}$ 3450–3250 $\nu_{C=O}$ 1620 | *1 |
| " | " | " | " |  | " | " | " | " | $\nu_{NH}$ 3350 $\nu_{C=O}$ 1635 | *1 |
| " | " | " | " |  | " | " | " | " | $\nu_{NH}$ 3350 $\nu_{C=O}$ 1640 | *1 |
| " | " | " | " |  | " | " | " | " | $\nu_{NH}$ 3350 $\nu_{C=O}$ 1640 | *1 |
| " | " | " | " | (see structure below) | " | " | " | " | $\nu_{NH}$ 3450–3250 $\nu_{C=O}$ 1620 | *1 |

TABLE 4-continued

Symbol in General Formula (I)

| R¹ | R² | R³ | R⁴ | R⁵ | A | n | Configuration* | Melting point (°C.) | IR (cm⁻¹) | Remarks |
|---|---|---|---|---|---|---|---|---|---|---|
| " | " | " | " | piperidine-N-CH with NHCO-(3,4,5-trimethoxyphenyl) | " | " | " | " | $\nu_{NH}$ 3500–3300<br>$\nu_{C=O}$ 1620 | *1 |
| " | " | " | " | 4-amino-piperidine·2HCl | $\{$ | " | " | " | $\nu_{NH}$ 3400<br>$\nu_{C=O}$ 1620 | *1 |
| " | " | " | " | 4-NHZ-piperidine | " | " | " | " | $\nu_{NH}$ 3290<br>$\nu_{C=O}$ 1710, 1620 | *1 |
| " | " | " | H | 2-methyl-2,5-dihydrofuran | —CH=CH—<br>(trans) | " | DL | 170–171 | $\nu_{NH}$ 3260<br>$\nu_{C=O}$ 1640, 1600 | *1 |
| " | H | " | " | " | —CH=CH—<br>(trans) | " | " | 206–207 | $\nu_{NH}$ 3305<br>$\nu_{C=O}$ 1645, 1610 | *1 |
| " | " | Me | " | " | —CH=CH—<br>(trans) | " | " | 218–220 | $\nu_{NH}$ 3290<br>$\nu_{C=O}$ 1640, 1605 | *2 |
| Et | Et | Et | Et | " | —CH=CH—<br>(trans) | " | " | 147–150 | $\nu_{NH}$ 3260<br>$\nu_{C=O}$ 1670, 1610 | *2 |
| Me | Me | " | " | " | —CH=CH—<br>(trans) | " | " | 168–170 | $\nu_{NH}$ 3300<br>$\nu_{C=O}$ 1660 | *1 |
| " | " | n-Pr | n-Pr | benzofuran-2-yl | —CH=CH—<br>(trans) | " | " | 163–165 | $\nu_{NH}$ 3260<br>$\nu_{C=O}$ 1640, 1610 | *1 |
| " | " | " | " | benzothiophen-2-yl | —CH=CH—<br>(trans) | " | " | 128–129 | $\nu_{NH}$ 3270<br>$\nu_{C=O}$ 1660, 1640, 1615 | *1 |

TABLE 4-continued

Symbol in General Formula (I)

| R¹ | R² | R³ | R⁴ | R⁵ | A | n | Configuration* | Melting point (°C.) | IR (cm⁻¹) | Remarks |
|---|---|---|---|---|---|---|---|---|---|---|
| " | " | " | " | (furan-Ph) | —CH=CH— (trans) | " | " | 132–133 | $\nu_{NH}$ 3290 $\nu_{C=O}$ 1665, 1630, 1620 | *1 |
| " | " | " | " | (furan-C₆H₄Cl) | —CH=CH— (trans) | " | " | 167–168 | $\nu_{NH}$ 3260 $\nu_{C=O}$ 1660, 1640, 1615 | *1 |
| " | " | " | " | (benzofuran-Me) | —CH=CH— (trans) | " | " | 132–134 | $\nu_{NH}$ 3250 $\nu_{C=O}$ 1640, 1610 | *1 |
| " | " | " | " | (Cl-benzofuran) | —CH=CH— (trans) | " | " | 123–127 | $\nu_{NH}$ 3275 $\nu_{C=O}$ 1660, 1638, 1612 | *1 |
| " | " | " | " | (OMe-benzofuran) | —CH=CH— (trans) | " | " | 104–108 | $\nu_{NH}$ 3260 $\nu_{C=O}$ 1610 | *1 |
| " | " | " | " | (OH-benzofuran) | —CH=CH— (trans) | " | " | 144–146 | $\nu_{NH}$ 3250 $\nu_{C=O}$ 1640, 1610 | *1 |
| " | " | n-Bu | " | (thiophene-Me) | —CH=CH— (trans) | " | " | 129–131 | $\nu_{NH}$ 3250 $\nu_{C=O}$ 1640, 1600 | *1 |
| " | " | " | n-Bu | (furan) | —CH=CH— (trans) | " | " | 124–126 | $\nu_{NH}$ 3250 $\nu_{C=O}$ 1650, 1610 | *1 |

TABLE 4-continued

Symbol in General Formula (I)

| $R^1$ | $R^2$ | $R^3$ | $R^4$ | $R^5$ | A | n | Configuration* | Melting point (°C.) | IR (cm$^{-1}$) | Remarks |
|---|---|---|---|---|---|---|---|---|---|---|
| " | " | " | " | benzofuranyl | —CH=CH— (trans) | " | " | 159–161 | $\nu_{NH}$ 3300 $\nu_{C=O}$ 1670, 1620 | *1 |
| " | " | " | " | tetrahydrofuranyl | —CH=CH— (trans) | " | " | 148–149 | $\nu_{NH}$ 3220 $\nu_{C=O}$ 1655, 1615 | *1 |
| " | " | " | " | benzofuranyl | —CH=CH— (trans) | " | " | 190–190.5 | $\nu_{NH}$ 3290 $\nu_{C=O}$ 1645, 1610 | *1 |
| " | " | " | tetrahydropyranyl | tetrahydrofuranyl | —CH=CH— (trans) | " | " | 169–171 | $\nu_{NH}$ 3300 $\nu_{C=O}$ 1660, 1620 | *1 |
| " | " | " | " | benzofuranyl | —CH=CH— (trans) | " | " | 178–180 | $\nu_{NH}$ 3300 $\nu_{C=O}$ 1630, 1610 | *1 |
| n-Pr | n-Pr | Me | Me | tetrahydrofuranyl | —CH=CH— (trans) | " | " | 116–119 | $\nu_{NH}$ 3250 $\nu_{C=O}$ 1660, 1620 | *1 |
| " | " | " | " | benzofuranyl | —CH=CH— (trans) | " | " | 156–157 | $\nu_{NH}$ 3250 $\nu_{C=O}$ 1630 | *1 |
| " | " | n-Pr | n-Pr | tetrahydrofuranyl | —CH=CH— (trans) | " | " | 121.5–123 | $\nu_{NH}$ 3240 $\nu_{C=O}$ 1670, 1625 | *2 |
| Me | Me | " | " | " | —CH=CH— (trans) | " | D | 133–134 | $\nu_{NH}$ 3260 $\nu_{C=O}$ 1670, 1640, 1610 | *1 |

TABLE 4-continued

Symbol in General Formula (I)

| $R^1$ | $R^2$ | $R^3$ | $R^4$ | $R^5$ | A | n | Configuration* | Melting point (°C.) | IR (cm$^{-1}$) | Remarks |
|---|---|---|---|---|---|---|---|---|---|---|
| " | " | " | " | " | —CH=CH— (trans) | " | L | 133–134 | $\nu_{NH}$ 3260 $\nu_{C=O}$ 1670, 1640, 1610 | *1 |
| " | " | " | " | " | —CH=CH— (trans) | 1 | DL | 150–151 | $\nu_{NH}$ 3260 $\nu_{C=O}$ 1660, 1635, 1610 | *1 |
| " | " | " | " | Bond | " | " | L | — | $\nu_{NH}$ 3290 $\nu_{C=O}$ 1610 | *1 |
| " | " | " | " | ⬡—CH$_2$NHZ (H) | " | 2 | L | 62–72 | $\nu_{NH}$ 3290 $\nu_{C=O}$ 1680, 1620 | *1 |
| " | " | " | " | ⬡—CH$_2$NH$_2$·HBr (H) | " | " | " | — | $\nu_{NH}$ 3400 $\nu_{C=O}$ 1620 | *1 |
| H | " | H | Me | furan | —CH=CH— (trans) | " | DL | 218–220 | $\nu_{NH}$ 3290 $\nu_{C=O}$ 1640, 1605 | *2 |
| " | Et | " | Et | " | —CH=CH— (trans) | " | " | 229–233 | $\nu_{NH}$ 3300 $\nu_{C=O}$ 1620 | *2 |
| " | Me | " | n-Pr | " | —CH=CH— (trans) | " | " | 206–207 | $\nu_{NH}$ 3305 | *1 |
| " | Et | " | " | " | —CH=CH— (trans) | " | " | 208–211 | $\nu_{NH}$ 3270 $\nu_{C=O}$ 1645, 1610 | *1 |
| " | H | " | " | " | —CH=CH— (trans) | " | " | 175–178 | $\nu_{NH}$ 3260 $\nu_{C=O}$ 1640, 1610 | *1 |
| " | n-Pr | " | i-Pr | " | —CH=CH— (trans) | " | " | 205–207 | $\nu_{NH}$ 3270 $\nu_{C=O}$ 1650, 1600 | *1 |
| " | i-Pr | " | n-Pr | " | —CH=CH— (trans) | " | " | 269–272 | $\nu_{NH}$ 3280 $\nu_{C=O}$ 1630, 1610 | *2 |
| " | n-Bu | " | n-Bu | " | —CH=CH— (trans) | " | " | 200–202 | $\nu_{NH}$ 3280 $\nu_{C=O}$ 1620 | *2 |
| " | " | " | i-Bu | " | —CH=CH— (trans) | " | " | 197–200 | $\nu_{NH}$ 3260 $\nu_{C=O}$ 1640, 1610 | *1 |
| " | i-Bu | " | t-Bu | " | —CH=CH— (trans) | " | " | 213–216 | $\nu_{NH}$ 3290 $\nu_{C=O}$ 1620 | *2 |
| " | t-Bu | " | n-Am | " | —CH=CH— (trans) | " | " | 105–108 | $\nu_{NH}$ 3300 $\nu_{C=O}$ 1650–1610 | *2 |
| " | n-Am | " | " | " | —CH=CH— (trans) | " | " | 182–185 | $\nu_{NH}$ 3280 $\nu_{C=O}$ 1620 | *2 |

TABLE 4-continued

| | | Symbol in General Formula (I) | | | | | Melting point (°C.) | IR (cm$^{-1}$) | Remarks |
|---|---|---|---|---|---|---|---|---|---|
| R$^1$ | R$^2$ | R$^3$ | R$^4$ | R$^5$ | A | n | Configuration* | | |
| " | i-Am | " | i-Am | " | —CH=CH— (trans) | " | " | 164–167 | $\nu_{NH}$ 3300 $\nu_{C=O}$ 1640, 1620 | *2 |
| " | n-Hex | " | n-Hex | " | —CH=CH— (trans) | " | " | 175–177 | $\nu_{NH}$ 3310 $\nu_{C=O}$ 1620 | *2 |
| " | cyclohexyl | " | cyclohexyl | " | —CH=CH— (trans) | " | " | 202–205 | $\nu_{NH}$ 3300 $\nu_{C=O}$ 1620 | *2 |
| " | CH$_2$CH=CH$_2$ | " | CH$_2$CH=CH$_2$ | " | —CH=CH— (trans) | " | " | 200–203 | $\nu_{NH}$ 3300 $\nu_{C=O}$ 1620 | *2 |
| " | CH$_2$CH$_2$Cl | " | CH$_2$CH$_2$Cl | " | —CH=CH— (trans) | " | " | 184–188 | $\nu_{NH}$ 3300 $\nu_{C=O}$ 1640, 1610 | *2 |
| " | CH$_2$C$_6$H$_5$ | " | CH$_2$C$_6$H$_5$ | " | —CH=CH— (trans) | " | " | 182–186 | $\nu_{NH}$ 3300 $\nu_{C=O}$ 1680, 1620 | *2 |
| " | CH$_2$CH$_2$OH | " | CH$_2$CH$_2$OH | " | —CH=CH— (trans) | " | " | 150–153 | $\nu_{NH}$ 3280 $\nu_{C=O}$ 1640, 1610 | |
| " | " | " | n-Pr | " | —CH=CH— (trans) | " | " | 165–167 | $\nu_{NH}$ 3280 $\nu_{C=O}$ 1630, 1600 | *1 |
| " | " | n-Pr | " | " | —CH=CH— (trans) | " | " | 97–100 | $\nu_{NH}$ 3250 $\nu_{C=O}$ 1660, 1600 | *1 |
| n-Pr | n-Pr | H | n-Pr | " | —CH=CH— (trans) | " | " | 123–124 | $\nu_{NH}$ 3280 $\nu_{C=O}$ 1650, 1605 | *1 |
| n-Bu | n-Bu | n-Bu | n-Bu | " | —CH=CH— (trans) | " | " | 78–80 | $\nu_{NH}$ 3260 $\nu_{C=O}$ 1670, 1650, 1610 | *2 |
| | H | H | | " | —CH=CH— (trans) | " | " | 217–220 | $\nu_{NH}$ 3280 $\nu_{C=O}$ 1630, 1610 | *1 |
| CH$_2$CH$_2$OMe | tetrahydropyranyl | " | " | " | —CH=CH— (trans) | " | " | 150–153 | $\nu_{NH}$ 3300, 3250 $\nu_{C=O}$ 1650, 1610 | *1 |
| CH$_2$CH$_2$OMe | H | " | CH$_2$CH$_2$OMe | " | —CH=CH— (trans) | " | " | 144–146 | $\nu_{NH}$ 3280 $\nu_{C=O}$ 1630, 1610 | *2 |
| H | " | " | n-Bu | " | —CH=CH— (trans) | " | " | 210–212 | $\nu_{NH}$ 3280 $\nu_{C=O}$ 1630, 1610 | *1 |

Note:
1: These compounds were obtained by production processes [A] to [C].
2: These compounds were obtained by production processes [A] to [D].

PREPARATION EXAMPLE 1

10 grams of DL-2-[β-(2-furyl)acrylamido]-$N^1,N^1,N^5,N^5$-tetramethyl-pentane-1,5-diamide, 140 g of lactose, 45 g of starch and 5 g of talc were mixed and then made into 1,000 capsules.

PREPARATION EXAMPLE 2

10 grams of DL-2-[β-(2-benzofuryl)acrylamido]-$N^5,N^5$-dimethyl-$N^1,N^1$-di(n-propyl)-pentane-1,5-diamide, 25 g of cornstarch, 10 g of crystalline cellulose, 100 g of a lactose and 1.5 g of magnesium stearate were mixed and then made into 1,000 tablets.

PREPARATION EXAMPLE 3

10 grams of DL-$N^1,N^5$-di-n-butyl-2-[β-(2-furyl)acrylamido]-pentane-1,5-diamide, 140 g of lactose, 45 g of starch and 5 g of talc were mixed and then made into 1,000 capsules.

PREPARATION EXAMPLE 4

10 grams of DL-$N^1,N^5$-di-n-butyl-2-[β-(2-furyl)acrylamido]-pentane-1,5-diamide, 25 g of cornstarch, 10 g of crystalline cellulose, 100 g of lactose and 1.5 g of magnesium stearate were mixed and then made into 1,000 tablets.

PREPARATION EXAMPLE 5

10 grams of DL-2-[β-(2-furyl)acrylamido]-$N^1,N^5$-di(isopropyl)-pentane-1,5-diamide, 140 g of lactose, 45 g of starch and 5 g of talc were mixed and then made into 1,000 capsules.

PREPARATION EXAMPLE 6

10 grams of DL-2-[β-(2-furyl)acrylamido]-$N^1,N^5$-di(isopropyl)-pentane-1,5-diamide, 25 g of cornstarch, 10 g of crystalline cellulose, 100 g of lactose and 1.5 g of magnesium stearate were mixed and then made into 1,000 tablets.

What is claimed is:

1. An N-acyl acidic amino acid diamide derivative represented by the general formula or a salt thereof:

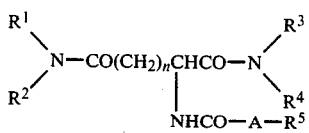

wherein each of $R^1$, $R^2$, $R^3$ and $R^4$, which may be the same or different, represents a hydrogen atom or a $C_{1-8}$alkyl, $C_{3-7}$cycloalkyl, $C_{2-4}$alkenyl, benzyl, phenethyl or naphthylmethyl group, or $R^1$ and $R^2$ and/or $R^3$ and $R^4$, when taken together with the respective adjacent nitrogen atom, form a pyrrolidinyl, piperidyl, piperazinyl or morpholinyl group, and $R^5$ represents a heterocyclic group selected from thienyl, furyl, pyrrolyl, imidazolyl, pyrazolyl, thiazolyl, isothiazolyl, oxazolyl, isoxazolyl, pyrrolidinyl, pyrrolinyl, imidazolidinyl, imidazolinyl, pyrazolidinyl, triazolyl, tetrazolyl, tetrahydrofuryl, pyranyl, pyridyl, pyrazinyl, pyrimidinyl, pyridazinyl, piperidyl, piperazinyl, morpholinyl, triazinyl, thiazinyl, benzothienyl, benzofuryl, isobenzofuryl, indolyl, isoindolyl, indazolyl, purinyl, quinolyl, isoquinolyl, naphthyridinyl, quinoxadinyl, chromanyl, indolinyl, isoindolinyl, chromenyl and 3,5-epoxy-1-cyclohexenyl, and $R^1$, $R^2$, $R^3$, $R^4$ and $R^5$ may be substituted by at least one substituent selected from halogen, hydroxyl, amino, carboxyl, $C_{1-8}$alkyl, oxo, $C_{1-8}$alkoxy, phenyl, naphthyl, chlorophenyl, benzyl, phenethyl, naphthylmethyl, (2,3,4- or 3,4,5-)trimethoxybenzyl, amino-$C_{1-4}$alkyl, di-$C_{1-4}$alkylamino-$C_{1-4}$alkyl, hydroxy-substituted $C_{1-4}$alkyl, $C_{1-5}$alkanoyloxy, styrylcarbonyl, 3,4,5-trimethoxystyrylcarbonyl, benzyloxycarbonylamino, benzyloxycarbonylaminomethyl, benzoylamino, 3,4,5-trimethoxybenzoylamino, pyrrolidinylcarbonylmethyl, piperidylcarbonylmethyl, piperazinylcarbonylmethyl and morpholinylcarbonylmethyl; A represents a bond or a $C_{1-5}$alkylene, $C_{2-5}$alkenylene or $C_{4-6}$alkadienylene group which may be substituted by at least one substituent selected from $C_{1-8}$alkyl groups hydroxyl group, phenyl group and naphthyl group; and n is 1, 2 or 3.

2. An N-acyl acidic amino acid diamide derivative or a salt thereof according to claim 1, wherein each of $R^1$ and $R^2$, which may be the same or different, represents a hydrogen atom or a $C_{1-8}$alkyl group.

3. An N-acyl acidic amino acid diamide derivative or a salt thereof according to claim 2, wherein each of $R^3$ and $R^4$, which may be the same or different, represents a hydrogen atom or a $C_{1-8}$alkyl group.

4. An N-acyl acidic amino acid diamide derivative or a salt thereof according to claim 2, wherein $R^3$ and $R^4$, when taken together with the adjacent nitrogen atom, may form a pyrrolidinyl, piperidyl, piperazinyl or morpholinyl group which may be substituted by the substituents defined in claim 2.

5. An N-acyl acidic amino acid diamide derivative or a salt thereof according to claim 4, wherein $R^3$ and $R^4$, when taken together with the adjacent nitrogen atom, form a pyrrolidinyl, piperidyl or morpholinyl group.

6. An N-acyl acidic amino acid diamide derivative or a salt thereof according to claim 1, wherein each of $R^1$, $R^2$, $R^3$ and $R^4$, which may be the same or different, represents a hydrogen atom or a $C_{3-7}$cycloalkyl, $C_{2-4}$alkenyl, benzyl, phenethyl or naphthyl group.

7. An N-acyl acidic amino acid diamide derivative or a salt thereof according to claim 2 or 3, wherein A represents $C_{2-5}$alkenylene which may be substituted by the substituents defined in claim 2.

8. An N-acyl acidic amino acid diamide derivative or a salt thereof according to claim 7, wherein A represents a vinylene group.

9. An N-acyl acidic amino acid diamide derivative or a salt thereof according to claim 8, wherein $R^5$ represents a furyl group.

10. An N-acyl acidic amino acid diamide derivative or a salt thereof according to claim 8 or 2 wherein n is 2.

11. 2-[β-(2-furyl)acrylamido]-$N^5$-methyl-$N^1,N^1$-di(n-propyl)-pentane-1,5-diamide.

12. 2-[β-(2-furyl)acrylamido]-$N^5,N^5$-dimethyl-$N^1,N^1$-di(n-propyl)-pentane-1,5-diamide.

13. 2-[β-(2-furyl)acrylamido]-$N^1,N^1,N^5,N^5$-tetramethyl-pentane-1,5-diamide.

14. 2-[β-(2-furyl)acrylamido]-$N^1,N^5$-di(n-propyl)-pentane-1,5-diamide.

15. $N^1,N^5$-di(n-butyl)-2-[β-(2-furyl)acrylamido]-pentane-1,5-diamide.

16. 2-[β-(2-furyl)acrylamido]-$N^1,N^5$-di(isoamyl)-pentane-1,5-diamide.

17. 2-[β-(2-furyl)acrylamido]-$N^1,N^5$-bis(3-methyl-2-butenyl)-pentane-1,5-diamide.

18. $N^1,N^5$-bis(3-acetoxypropyl)-2-[β-(2-furyl)acrylamido]-pentane-1,5-diamide.

19. 2-[β-(2-furyl)acrylamido]-$N^1,N^5$-di(isopropyl)-pentane-1,5-diamide.

20. $N^1,N^1,N^5,N^5$-tetra-n-butyl-2-[β-(2-furyl)acrylamido]-pentane-1,5-diamide.

21. 2-[β-2-(furyl)acrylamido]-$N^1,N^1,N^5,N^5$-tetra(n-propyl)-pentane-1,5-diamide.

22. An anti-ulcer agent comprising an anti-ulcer effective amount of the N-acyl acidic amino acid diamide derivative or a salt thereof according to claim 1 in a pharmaceutically acceptable carrier.

* * * * *